(12) United States Patent
Krebs et al.

(10) Patent No.: US 8,362,006 B2
(45) Date of Patent: Jan. 29, 2013

(54) PROCESSES FOR MAKING ZILPATEROL AND SALTS THEREOF

(75) Inventors: Oliver Krebs, Langenfeld (DE); Stephane Dubuis, Visp (CH)

(73) Assignee: Intervet International B.V., Boxmeer (NL)

( * ) Notice: Subject to any disclaimer, the term of this patent is extended or adjusted under 35 U.S.C. 154(b) by 414 days.

(21) Appl. No.: 12/450,253

(22) PCT Filed: Mar. 28, 2008

(86) PCT No.: PCT/EP2008/053711
§ 371 (c)(1),
(2), (4) Date: Sep. 18, 2009

(87) PCT Pub. No.: WO2008/119754
PCT Pub. Date: Oct. 9, 2008

(65) Prior Publication Data
US 2010/0121050 A1    May 13, 2010

Related U.S. Application Data

(60) Provisional application No. 60/920,885, filed on Mar. 31, 2007, provisional application No. 60/909,611, filed on Apr. 2, 2007.

(30) Foreign Application Priority Data

Apr. 3, 2007   (EP) .................................... 07105551

(51) Int. Cl.
*C07D 487/06*   (2006.01)
*C07D 235/26*   (2006.01)

(52) U.S. Cl. .................................. 514/214.02; 540/579

(58) Field of Classification Search ............. 514/214.02; 540/579
See application file for complete search history.

(56) References Cited

U.S. PATENT DOCUMENTS

| 4,585,770 | A | 4/1986 | Frechet et al. |
| 5,731,028 | A | 3/1998 | Chevremont et al. |
| 2006/0040950 | A1 | 2/2006 | Janssens et al. |
| 2008/0267942 | A1* | 10/2008 | Boyle et al. .................. 424/94.1 |
| 2010/0173892 | A1* | 7/2010 | Almena-Perea et al. 514/214.02 |

FOREIGN PATENT DOCUMENTS

| WO | WO 2004/056799 A | 7/2004 |
| WO | WO 2008/119754 A1 | 10/2008 |

OTHER PUBLICATIONS

Salaski et al., Synthesis of imidazobenzazepinthiones: A new series of HIV-1 reverse transcriptase inhibitors, Tetrahedron Letters, Feb. 27, 1995, pp. 1387-1390, vol. 36, No. 9, Elsevier, Amsterdam, NL.
PCT Written Opinion of the International Searching Authority, PCT/EP2008/053711, Oct. 6, 2009.
PCT International Search Report, PCT/EP2008/053711, Jan. 22, 2008.
PCT International Search Report; PCT/EP2008/053711 dated Aug. 5, 2008.

* cited by examiner

*Primary Examiner* — Brenda Coleman

(57) ABSTRACT

This invention generally relates to processes for making zilpaterol and salts thereof, as well as processes for making intermediates that, inter alia, may be used to make zilpaterol and salts thereof. The zilpaterol and salts prepared in accordance with this invention can be used to increase the rate of weight gain, improve feed efficiency, and/or increase carcass leanness in livestock, poultry, and fish.

15 Claims, No Drawings

PROCESSES FOR MAKING ZILPATEROL AND SALTS THEREOF

CROSS-REFERENCE TO RELATED PATENT APPLICATIONS

This patent is a national stage entry under 35 U.S.C. §371 of PCT/EP2008/053711 filed Mar. 28, 2008 which claims priority to U.S. Patent Appl. No. 60/920,885 (filed Mar. 31, 2007); U.S. Patent Appl. No. 60/909,611 (filed Apr. 2, 2007); and EP Patent Appl. No. EP07105551.1 (filed Apr. 3, 2007). The entire text of each of these patent applications is incorporated by reference into this patent.

FIELD OF THE INVENTION

This invention generally relates to processes for making zilpaterol and salts thereof, as well as processes for making intermediates that, inter alia, may be used to make zilpaterol and salts thereof. This invention also relates to methods of treatment using zilpaterol and salts prepared in accordance with this invention to increase the rate of weight gain, improve feed efficiency, and/or increase carcass leanness in livestock, poultry, and fish.

BACKGROUND OF THE INVENTION

Zilpaterol is a known adrenergic β-2 agonist having the following structure:

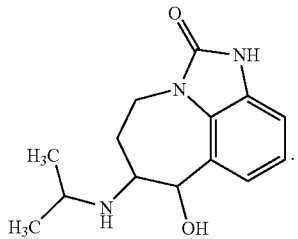 [SMILES: CC(C)NC1CCn2c(=O)[nH]c3cccc(c32)C1O]

The IUPAC name for zilpaterol is 4,5,6,7-tetrahydro-7-hydroxy-6-(isopropylamino)imidazo[4,5,1-jk]-[1]benzazepin-2(1H)-one. The Chemical Abstracts name for zilpaterol is 4,5,6,7-tetrahydro-7-hydroxy-6-[(1-methyl-ethyl) amino]-imidazo [4,5,1-jk][1]benzazepin-2(1H)-one.

It is well known that zilpaterol, various zilpaterol derivatives, and various pharmaceutically acceptable acid addition salts of zilpaterol and its derivatives may, for example, be used to increase the rate of weight gain, improve feed efficiency (i.e., decrease the amount of feed per amount of weight gain), and/or increase carcass leanness (i.e., increase protein content in carcass soft tissue) in livestock, poultry, and/or fish. In U.S. Pat. No. 4,900,735, for example, Grandadam describes zootechnical compositions of racemic trans zilpaterol and salts thereof that may be used to increase the weight and meat quality of warm-blooded animals, including cattle, pigs, and poultry. And U.S. Patent Appl. Publ. US2005/0284380 describes use of an ionophore/macrolide/zilpaterol dosing regimen to increase beef production, reduce feed intake while maintaining beef production, and reduce incidences of liver abscess in cattle.

Methods for making zilpaterol are known in the art. For example, in U.S. Pat. No. 4,585,770, Fréchet et al. describe compounds encompassed by a genus characterized as 6-amino-7-hydroxy-4,5,6,7-tetrahydro-imidazo[4,5,1-jk][1]-benzazepin-2[1H]-one derivatives and pharmaceutically acceptable acid addition salts thereof. The derivatives correspond in structure to the following formula:

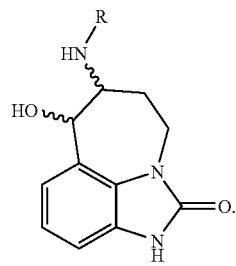

Here, R can be various substituents, and the wavy lines indicate that the bonds to the 6-amino and 7-OH groups have the trans configuration. This genus encompasses racemic trans zilpaterol when R is isopropyl.

The methods reported in U.S. Pat. No. 4,585,770 use 4,5-dihydro-imidazo[4,5,1-jk][1]benzazepin-2,6,7[1H]-trione-6-oxime as an intermediate. This compound corresponds in structure to the following formula:

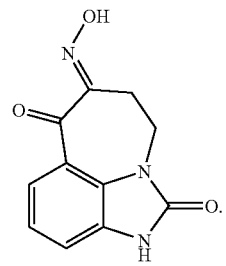 [SMILES: O=C1/C(=N/O)CCn2c(=O)[nH]c3cccc1c32]

As indicated in U.S. Pat. No. 4,585,770, 4,5-dihydro-imidazo[4,5,1-jk][1]benzazepin-2,6,7[1H]-trione-6-oxime may be formed from starting materials that have been long known in the art. U.S. Pat. No. 4,585,770 illustrates the use of two such starting materials. In both examples, the starting materials are used to form 5,6-dihydro-imidazo[4,5,1-jk][1]benzazepin-2,7-[1H,4H]-dione, which, in turn, may be used to make 4,5-dihydro-imidazo[4,5,1-jk][1]benzazepin-2,6,7[1H]-trione-6-oxime.

In one of the examples in U.S. Pat. No. 4,585,770, the starting material is 1,3-dihydro-1-(1-methylethenyl)-2H-benzimidazol-2-one, which is described in *J. Chem. Soc. Perkins*, p. 261 (1982):

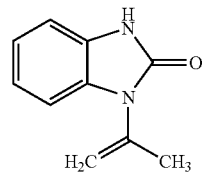

1,3-dihydro-1-(1-methylethenyl)-2H-benzimidazol-2-one

U.S. Pat. No. 4,585,770 indicates that 1,3-dihydro-1-(1-methylethenyl)-2H-benzimidazol-2-one may be reacted with an alkyl 4-halobutyrate (i.e., $R^A$—$(CH_2)_3$—$COOR^B$ (wherein $R^A$ is Cl, Br, or I; and $R^B$ is $C_1$-$C_4$-alkyl), such as methyl or ethyl 4-bromobutyrate) and a base (e.g., an alkali metal) to form a butanoate, which, in turn may be hydrolyzed with an acid (e.g., $H_2SO_4$) in an alkanol (e.g., methanol or ethanol) to remove the methylethenyl substituent. The hydrolysis product then may be subjected to saponification by reacting it with a base (e.g., NaOH or KOH) in an alkanol to form a carboxylic acid. Subsequently, the carboxylic-acid-terminated side chain may be cyclized to form 5,6-dihydro-imidazo[4,5,1-jk][1]benzazepin-2,7-[1H,4H]-dione by reacting the carboxylic acid with thionyl chloride to obtain a chloride, and then treating the chloride with a Lewis acid (e.g., aluminum chloride) in an organic solvent (e.g., methylene chloride or dichloroethane):

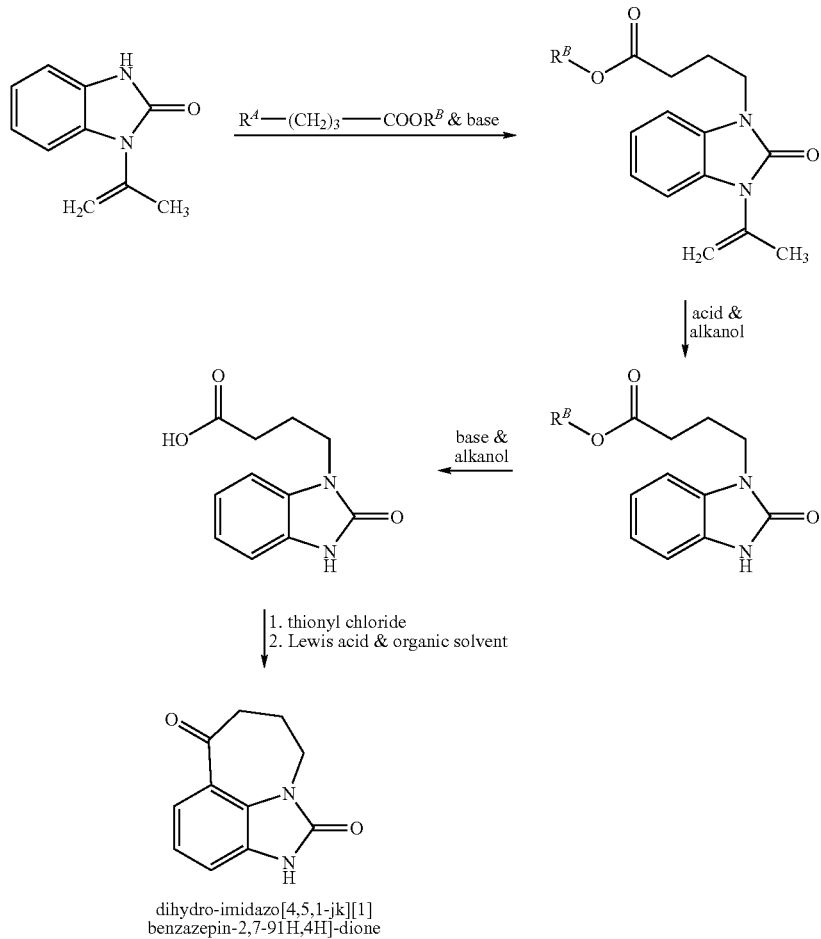

dihydro-imidazo[4,5,1-jk][1]
benzazepin-2,7-91H,4H]-dione

See U.S. Pat. No. 4,585,770, col. 4, line 3 to col. 5, line 14; and Example 14, col. 12, lines 1-68.

In another example in U.S. Pat. No. 4,585,770, the starting material is 1,3-dihydro-1-benzyl-2H-benzimidazol-2-one, which is described in *Helv.*, Vol 44, p. 1278 (1961):

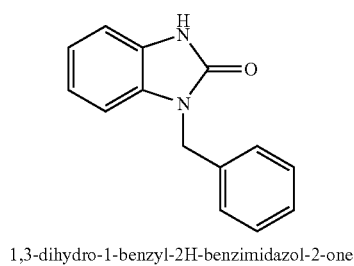 [SMILES: O=c1[nH]c2ccccc2n1Cc1ccccc1]

1,3-dihydro-1-benzyl-2H-benzimidazol-2-one

U.S. Pat. No. 4,585,770 indicates that the 1,3-dihydro-1-benzyl-2H-benzimidazol-2-one may be reacted with ethyl 4-bromobutyrate and sodium hydride to form 1,3-dihydro-2-oxo-3-benzyl-1H-benzimidazol-1-butanoate, which, in turn may be subjected to saponification by reacting it with methanolic NaOH to form 1,3-dihydro-2-oxo-3-benzyl-1H-benzimidazol-1-butanoic acid. The butanoic acid side chain may then be cyclized by reacting the 1,3-dihydro-2-oxo-3-benzyl-1H-benzimidazol-1-butanoic acid with thionyl chloride to obtain a chloride, and then treating the chloride with aluminum chloride in dichloroethane. The cyclized product, in turn, may be hydrolyzed using o-phosphoric acid in phenol to form 5,6-dihydro-imidazo[4,5,1-jk][1]benzazepin-2,7-[1H, 4H]-dione. See U.S. Pat. No. 4,585,770, Example 1, Steps A-D, col. 6, line 10 to col. 7, line 35.

Using the methods reported in U.S. Pat. No. 4,585,770, 5,6-dihydro-imidazo[4,5,1-jk][1]benzazepin-2,7-[1H,4H]-dione may be reacted with an alkyl nitrite (e.g., tert-butyl nitrite or isoamyl nitrite), in the presence of a base or acid (e.g., HCl), to form 4,5-dihydro-imidazo[4,5,1-jk][1]benzazepin-2,6,7[1H]-trione-6-oxime. The 4,5-dihydro-imidazo[4,5,1-jk][1]benzazepin-2,6,7[1H]-trione-6-oxime, in turn, is reduced via catalytic hydrogenation (with, for example, hydrogen in the presence of palladium on carbon) or sodium borohydride to form racemic trans 6-amino-7-hydroxy-4,5,6,7-tetrahydro-imidazo[4,5,1-jk][1]-benzazepin-2[1H]-one:

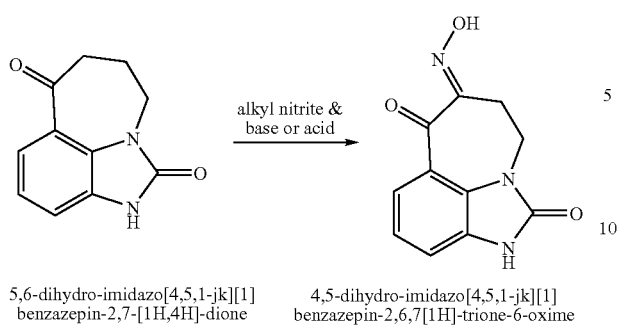

5,6-dihydro-imidazo[4,5,1-jk][1]
benzazepin-2,7-[1H,4H]-dione 4,5-dihydro-imidazo[4,5,1-jk][1]
benzazepin-2,6,7[1H]-trione-6-oxime catalytic hydrogenation
and/or sodium borohydride

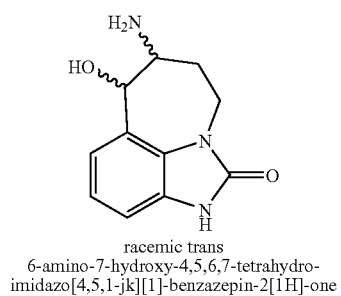

racemic trans
6-amino-7-hydroxy-4,5,6,7-tetrahydro-
imidazo[4,5,1-jk][1]-benzazepin-2[1H]-one In the illustrative example in U.S. Pat. No. 4,585,770, the 4,5-dihydro-imidazo[4,5,1-jk][1]benzazepin-2,6,7[1H]-trione-6-oxime is converted into racemic trans 6-amino-7-hydroxy-4,5,6,7-tetrahydro-imidazo[4,5,1-jk][1]-benzazepin-2[1H]-one in two steps: the 4,5-dihydro-imidazo[4,5,1-jk][1]benzazepin-2,6,7[1H]-trione-6-oxime is first reacted with $H_2$ in the presence of Pd-on-carbon, and, then, after filtration, the hydrogenation product is reacted with sodium borohydride. See U.S. Pat. No. 4,585,770, col. 2, line 15 to col. 4, line 2; and Example 1, Steps E & F, col. 7, line 38 to col. 8, line 3.

U.S. Pat. No. 4,585,770 reports that the trans stereoisomers of 6-amino-7-hydroxy-4,5,6,7-tetrahydro-imidazo[4,5,1-jk][1]-benzazepin-2[1H]-one may be alkylated with acetone in the presence of a reducing agent (e.g., an alkali metal borohydride or cyanoborohydride, such as sodium cyanoborohydride) to form racemic trans zilpaterol:

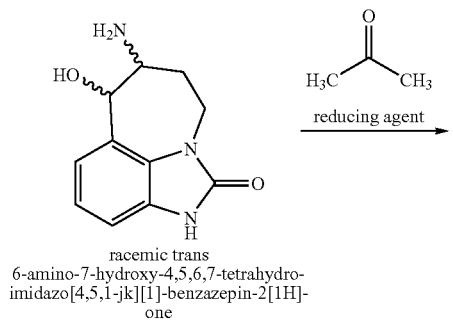

racemic trans
6-amino-7-hydroxy-4,5,6,7-tetrahydro-
imidazo[4,5,1-jk][1]-benzazepin-2[1H]-
one reducing agent

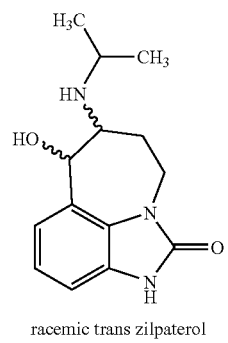

racemic trans zilpaterol

See U.S. Pat. No. 4,585,770, col. 2, line 46 to col. 4, line 2; and Example 13, col. 11, lines 41-68.

In view of the importance of zilpaterol and its salts in animal production, there continues to be a need for cost-effective, high-yield processes for making zilpaterol and its salts. The following disclosure addresses this need.

SUMMARY OF THE INVENTION

This invention relates to processes for making zilpaterol and salts thereof. Such processes include processes for making zilpaterol and the salts themselves, as well as processes for making compounds that, inter alia, may be used as intermediates for making zilpaterol and salts thereof.

Briefly, this invention is directed, in part, to a process for making zilpaterol or a salt thereof (e.g., a pharmaceutically acceptable salt). The process comprises making chloro 2,3-dihydro-2-oxo-1H-benzimidazol-1-butanoate (or a salt thereof) by a process comprising reacting 4-(2-oxo-2,3-dihydrobenzimidazol-1-yl)butyric acid (or a salt thereof) with at least one chlorinating agent, such as oxalyl chloride, phosgene, and/or triphosgene Alternatively (or additionally), the process comprises making 4,5-dihydro-imidazo[4,5,1-jk][1]benzazepin-2,6,7[1H]-trione-6-oxime (or a salt thereof) by a process comprising reacting 8,9-dihydro-2H,7H-2,9a-diazabenzo[cd]azulene-1,6-dione (or a salt thereof) with an inorganic nitrite (e.g., a nitrite salt, such as $NaNO_2$).

This invention also is directed, in part, to a process for making chloro 2,3-dihydro-2-oxo-1H-benzimidazol-1-butanoate or a salt thereof. This process comprises reacting 4-(2-oxo-2,3-dihydrobenzimidazol-1-yl)butyric acid (or a salt thereof) with at least one chlorinating agent, such as oxalyl chloride, phosgene, and/or triphosgene.

This invention also is directed, in part, to a process for making 8,9-dihydro-2H, 7H-2,9a-diazabenzo[cd]azulene-1,6-dione or a salt thereof. This process comprises making chloro 2,3-dihydro-2-oxo-1H-benzimidazol-1-butanoate (or a salt thereof) by a process comprising reacting 4-(2-oxo-2,3-dihydrobenzimidazol-1-yl)butyric acid (or a salt thereof) with at least one chlorinating agent, such as oxalyl chloride, phosgene, or triphosgene. In addition, the process comprises reacting chloro 2,3-dihydro-2-oxo-1H-benzimidazol-1-butanoate (or a salt thereof) with a Lewis acid (e.g., $AlCl_3$).

This invention also is directed, in part, to a process for making 4,5-dihydro-imidazo[4,5,1-jk][1]benzazepin-2,6,7[1H]-trione-6-oxime or a salt thereof. This process comprises reacting 8,9-dihydro-2H,7H-2,9a-diazabenzo[cd]azulene-1,6-dione (or a salt thereof) with an inorganic nitrite.

This invention also is directed, in part, to a method of feeding an animal. This method comprises feeding to an animal (e.g., a bovine animal, a swine animal, or a bird) zilpaterol or a salt thereof made by a process of this invention.

Such feeding methods may be used, for example, to increase the animal's rate of weight gain, improve the animal's feed efficiency, and/or increase the animal's carcass leanness.

This invention also is directed, in part, to a use of zilpaterol or a salt thereof, made by a process of this invention, to make a medicament. Uses for such a medicament include increasing an animal's rate of weight gain, improving an animal's feed efficiency, and/or increasing an animal's carcass leanness.

Further benefits of Applicants' invention will be apparent to one skilled iii the art from reading this specification.

DETAILED DESCRIPTION OF PREFERRED EMBODIMENTS

This detailed description of preferred embodiments is intended only to acquaint others skilled in the art with Applicants' invention, its principles, and its practical application so that others skilled in the art may adapt and apply the invention in its numerous forms, as they may be best suited to the requirements of a particular use. This detailed description and its specific examples, while indicating preferred embodiments of this invention, are intended for purposes of illustration only. This invention, therefore, is not limited to the preferred embodiments described in this specification, and may be variously modified.

A. Synthesis of Zilpaterol and Salts Thereof

A-1. Preparation of chloro 2,3-dihydro-2-oxo-1H-benzimidazol-1-butanoate

In some embodiments, the zilpaterol or salt synthesis begins by or includes preparing chloro 2,3-dihydro-2-oxo-1H-benzimidazol-1-butanoate:

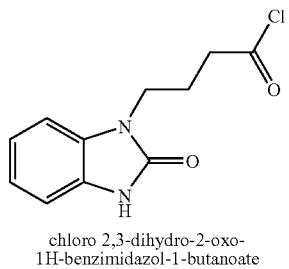 [SMILES: O=C(Cl)CCCn1c(=O)[nH]c2ccccc21]

chloro 2,3-dihydro-2-oxo-
1H-benzimidazol-1-butanoate

In some such embodiments, for example, the chloro 2,3-dihydro-2-oxo-1H-benzimidazol-1-butanoate is prepared from 4-(2-oxo-2,3-dihydrobenzimidazol-1-yl)butyric acid and at least one chlorinating agent. In some such embodiments, the chlorinating agent comprises oxalyl chloride:

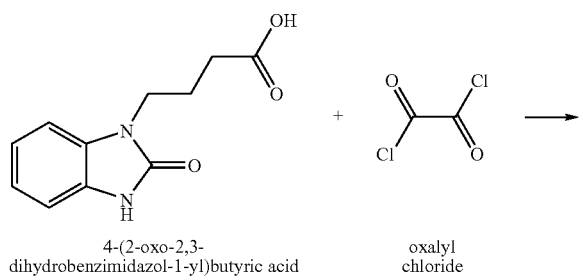

4-(2-oxo-2,3-
dihydrobenzimidazol-1-yl)butyric acid oxalyl
chloride

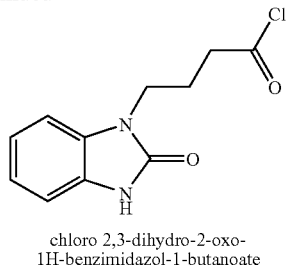

chloro 2,3-dihydro-2-oxo-
1H-benzimidazol-1-butanoate

In other embodiments, the chlorinating agent alternatively or additionally comprises, for example, phosgene or triphosgene:

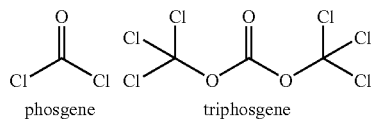

phosgene triphosgene

The 4-(2-oxo-2,3-dihydrobenzimidazol-1-yl)butyric acid reagent (also known as "2,3-dihydro-2-oxo-1H-benzimidazol-1-butanoic acid") may be obtained from a commercial vendor (to the extent any exist), or prepared from commercially available ingredients using, for example, methods known in the art. As indicated above in the Background of the Invention section, such methods include those described in U.S. Pat. No. 4,585,770 (the full text of U.S. Pat. No. 4,585,770 is incorporated by reference into this patent).

The amount of chlorinating agent may vary. In general, it is preferable to use an excess of chlorinating agent. In some embodiments, for example, the amount of chlorinating agent (e.g., oxalyl chloride) charged to the reactor is from about 1.05 to about 1.15 equivalents (or from about 1.05 to about 1.11 equivalents, or from about 1.08 to about 1.10 equivalents), based on moles of 4-(2-oxo-2,3-dihydrobenzimidazol-1-yl)butyric acid. Although it is contemplated that smaller amounts than the above ranges may be used, such amounts may coincide with reduced conversion. And, although it is contemplated that greater amounts than the above ranges may be used, such amounts may coincide with production of undesirable byproducts.

This reaction typically takes place in the presence of a catalyst. One such suitable catalyst comprises N,N-dimethylformamide ("DMF"). In general, at least a catalytic amount of DMF is charged to the reactor. In some embodiments, the amount of DMF charged to the reactor is from about 0.08 to about 0.22 (or from about 0.10 to about 0.14) equivalents, based on moles of 4-(2-oxo-2,3-dihydrobenzimidazol-1-yl) butyric acid. To illustrate, in some embodiments, the amount of DMF is about 0.11 equivalents. Although it is contemplated that smaller amounts than the above ranges may be used, such amounts may coincide with reduced conversion. And, although it is contemplated that greater amounts than the above ranges may be used, such amounts may coincide with production of undesirable byproducts.

This reaction typically is conducted in the presence of one or more solvents. In some embodiments, the solvent comprises one or more non-polar solvents. One such suitable solvent comprises dichloromethane. In some embodiments, the amount of solvent (e.g., dichloromethane) is from about 6.0 to about 9 L (or from about 6.8 to about 7.6 L) per kilogram of 4-(2-oxo-2,3-dihydrobenzimidazol-1-yl)butyric acid). To illustrate, in some embodiments, the amount of solvent is about 7.2 L per kilogram of 4-(2-oxo-2,3-dihydrobenzimidazol-1-yl)butyric acid.

This reaction may be conducted over a wide range of temperatures. In some embodiments, for example, the reaction is conducted at a temperature of from about 5 to about 25° C., from about 10 to about 25° C., from about 10 to about 20° C., or from about 15 to about 20° C. Although it is contemplated that lesser temperatures than the above ranges may be used, such temperatures may coincide with slower reaction rates. And, although it is contemplated that greater temperatures than the above ranges may be used, such temperatures may coincide with undesirable losses of solvent, particularly when the solvent is dichloromethane.

This reaction may be conducted under various atmospheres. In some embodiments, for example, the reaction is conducted under an inert atmosphere. In general, an "inert atmosphere" is an atmosphere that is non-reactive with the reagents, products, any other ingredients in the reaction mixture, or the reactor over the period in which the reaction is conducted. One such atmosphere, for example, comprises $N_2$. In some such embodiments, the atmosphere consists of (or consists essentially of) $N_2$.

This reaction may be conducted over a wide range of pressures, including atmospheric pressure, less than atmospheric pressure, and greater than atmospheric pressure. It is typically preferred, however, to conduct the reaction at about atmospheric pressure.

This reaction may be conducted with various reactor types. In some embodiments, for example, the reactor is a stirred-tank reactor. Glass and glass-lined reactors are often preferred, although any composition stable when exposed to the reaction mixture may be used. The agitation (e.g., stirring) of the reaction mixture preferably is maintained at a rate that minimizes (or, more preferably, essentially or completely avoids) any crusting of the 4-(2-oxo-2,3-dihydrobenzimidazol-1-yl)butyric acid reagent on the walls of the reactor. In some embodiments using a stirred-tank reactor, the stirring rate before and while the chlorinating agent is charged is slower relative to the stirring rate after the chlorinating agent has been charged. The stirring rate during the charging of the chlorinating agent, however, preferably is not so slow as to adversely affect conversion or disadvantageously delay gas evolution.

The reaction time for this reaction may depend on various factors including, for example, the reaction temperature, characteristics of the solvent, relative amounts of the ingredients, and the desired conversion. In a batch reactor, the reaction time is generally at least about 1 minute, typically at least about 5 minutes, and more typically at least about 1 hour. In some embodiments, for example, the reaction time is from about 1 hour to about 32 days, or from about 2 to about 7 hours. To illustrate, in some embodiments, the total reaction time is about 4 hours.

In some embodiments, the reaction time includes an extended period over which the chlorinating agent is charged to the reactor. In some such embodiments, for example, the chlorinating agent is charged to the reactor over a period of from about 15 minutes to about 10 hours, from about 1 to about 3 hours, or from about 1 to about 2 hours. Although it is contemplated that shorter time periods than the above ranges may be used, such time periods may coincide with rapid gas evolution, which, in turn, may cause an undesirable loss of solvent (particularly when the solvent comprises dichloromethane). And, although it is contemplated that greater time periods than the above ranges may be used, such periods may coincide with undesirable decomposition of the chloro 2,3-dihydro-2-oxo-1H-benzimidazol-1-butanoate product, as well as inefficient use of equipment and manpower.

In some embodiments wherein the chlorinating agent is charged over an extended period, the reaction mixture is subsequently maintained (or "aged"), typically while being agitated (e.g., stirred), for an additional period. In some embodiments, the additional period is from about 45 minutes to about 31 days, from about 1 to about 4 hours, or from about 1 to about 2 hours. Often, this additional period is conducted using the same reaction conditions (e.g., temperature, pressure, and/or stirring rate) as during the charging of the chlorinating agent. The conditions, however, also may be different. To illustrate, in some embodiments, the chlorinating agent is charged at a temperature of about 15° C., and then the mixture is aged at about 20° C. Although it is contemplated that shorter time periods than the above ranges may be used, such time periods may coincide with reduced conversion. And, although it is contemplated that greater time periods than the above ranges may be used, such periods may coincide with production of undesirable impurities (such as from the decomposition of the chloro 2,3-dihydro-2-oxo-1H-benzimidazol-1-butanoate product), as well as inefficient use of equipment and manpower.

Under the above conditions, the chloro 2,3-dihydro-2-oxo-1H-benzimidazol-1-butanoate product is generally in solution. It is contemplated that this product may be precipitated and purified or isolated using, for example, various methods known in the art. In general, however, the product is used in the next step without precipitating, purifying, or isolating it. In some such embodiments, the product mixture is used within 31 days, within 24 days, or within 9 days. Use of older product mixtures may coincide with undesirable chloro 2,3-dihydro-2-oxo-1H-benzimidazol-1-butanoate decomposition. In addition, these time ranges assume that the product mixture is not exposed to temperatures exceeding about 6° C. To the extent the product mixture is exposed to temperatures greater than about 6° C. (and particularly temperatures greater than about 25° C.), undesirable product decomposition may occur sooner.

A-2. Preparation of 8,9-dihydro-2H,7H-2,9a-diazabenzo[cd]azulene-1,6-dione

In some embodiments, the synthesis of zilpaterol or a salt thereof begins by or includes preparing 8,9-dihydro-2H,7H-2,9a-diazabenzo[cd]azulene-1,6-dione:

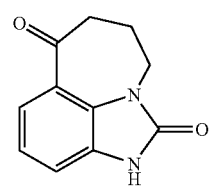

8,9-dihydro-2H,7H-2,9a-diazabenzo[cd]azulene-1,6-dione

In some embodiments, the 8,9-dihydro-2H,7H-2,9a-diazabenzo[cd]azulene-1,6-dione (also known as "5,6-dihydroimidazo[4,5,1-jk][1]-benzazepin-2,7-(1H,4H)-dione") is prepared by, for example, reacting chloro 2,3-dihydro-2-oxo-1H-benzimidazol-1-butanoate with a Lewis acid via a two reactions (i.e., a Friedel-Crafts reaction, and then a hydrolysis):

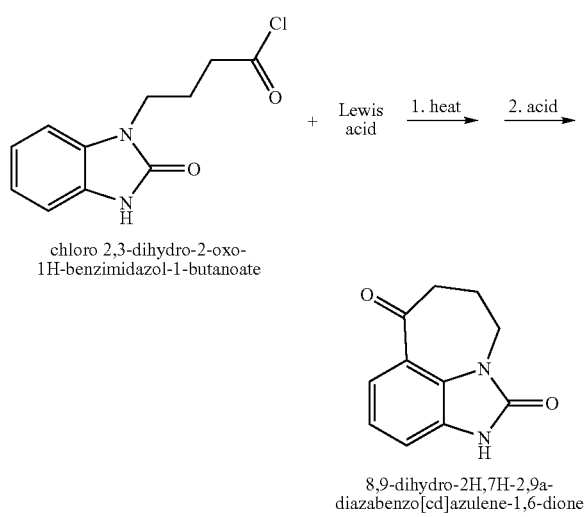

chloro 2,3-dihydro-2-oxo-1H-benzimidazol-1-butanoate 8,9-dihydro-2H,7H-2,9a-diazabenzo[cd]azulene-1,6-dione The chloro 2,3-dihydro-2-oxo-1H-benzimidazol-1-butanoate used in the above reaction may be obtained from a commercial vendor (to the extent any exist), prepared using a process discussed above in Section A-1, or prepared using a different process. In some embodiments, for example, the chloro 2,3-dihydro-2-oxo-1H-benzimidazol-1-butanoate is prepared by a process described in U.S. Pat. No. 4,585,770 that uses thionyl chloride as the chlorinating agent to convert the 4-(2-oxo-2,3-dihydrobenzimidazol-1-yl)butyric acid to chloro 2,3-dihydro-2-oxo-1H-benzimidazol-1-butanoate. In other embodiments, the chloro 2,3-dihydro-2-oxo-1H-benzimidazol-1-butanoate is prepared using $PCl_5$ as the chlorinating agent to convert the 4-(2-oxo-2,3-dihydrobenzimidazol-1-yl)butyric acid to chloro 2,3-dihydro-2-oxo-1H-benzimidazol-1-butanoate. In some preferred embodiments, the chloro 2,3-dihydro-2-oxo-1H-benzimidazol-1-butanoate is prepared using a process and chlorinating agents discussed above in Section A-1. Use of the chlorinating agents discussed in Section A-1 (particularly oxalyl chloride) instead of, for example, thionyl chloride or $PCl_5$, tends to coincide with fewer difficult-to-remove impurities. Use of thionyl chloride, for example, tends to produce sulfur impurities. And $PCl_5$ tends to produce phosphorus impurities. Removal of such impurities, in turn, tends to reduce the yield of the desired product.

Although it is contemplated that various Lewis acids (or combinations thereof) are suitable for this reaction, the Lewis acid preferably is aluminum chloride ("$AlCl_3$"). The amount of Lewis acid charged to the reactor may vary. In general, it is preferable to use an excess of the Lewis acid. In some embodiments, for example, the amount of Lewis acid (e.g., $AlCl_3$) charged to the reactor is from about 2.8 to about 4.0 equivalents (or from about 3.0 to about 3.6 equivalents), based on moles of chloro 2,3-dihydro-2-oxo-1H-benzimidazol-1-butanoate. To illustrate, in some embodiments, the amount of Lewis acid charged to the reactor is about 3.3 equivalents, based on moles of chloro 2,3-dihydro-2-oxo-1H-benzimidazol-1-butanoate. In some embodiments wherein the chloro 2,3-dihydro-2-oxo-1H-benzimidazol-1-butanoate is prepared in accordance with Section A-1, the amount of Lewis acid used in the Friedel-Crafts reaction is from about 2.8 to about 4.0 equivalents (or from about 3.0 to about 3.6 equivalents), based on the moles of 4-(2-oxo-2,3-dihydrobenzimidazol-1-yl)butyric acid used in the Section A-1 reaction. To illustrate, in some embodiments, the amount of Lewis acid charged to the reactor is about 3.3 equivalents, based on the moles of 4-(2-oxo-2,3-dihydrobenzimidazol-1-yl)butyric acid used in the Section A-1 reaction. Although it is contemplated that smaller amounts of aluminum chloride than the above ranges may be used, such amounts may coincide with reduced conversion and/or production of undesirable byproducts. And, although it is contemplated that greater amounts of aluminum chloride may be used, such amounts may coincide with losses in throughput during the subsequent hydrolysis.

The Friedel-Crafts reaction typically is conducted in the presence of one or more solvents. In some embodiments, for example, the solvent comprises one or more non-polar solvents. In some embodiments wherein the chloro 2,3-dihydro-2-oxo-1H-benzimidazol-1-butanoate reagent is prepared in accordance with Section A-1, the solvent is the same as the solvent used in Section A-1. One such suitable solvent comprises dichloromethane. As will be discussed below, the solvent (e.g., dichloromethane) used in the Friedel-Crafts reaction may be removed before, during, and/or after the hydrolysis via, for example, distillation. Thus, in some embodiments, the solvent has a boiling point that is Suitable for such removal.

The total amount of this solvent used for this reaction may vary. In some embodiments, the amount of solvent (e.g., dichloromethane) is about 11.1 L per kilogram of chloro 2,3-dihydro-2-oxo-1H-benzimidazol-1-butanoate. In some embodiments when the chloro 2,3-dihydro-2-oxo-1H-1-benzimidazol-1-butanoate reagent is prepared in accordance with Section A-1, the final product mixture from Section A-1 (including any solvent, e.g., dichloromethane) is used in the Friedel-Crafts reaction. In some such embodiments, the total amount of the solvent used in the Friedel-Crafts reaction (including the solvent from the Section A-1 reaction plus any solvent added for the Friedel-Crafts reaction) is about 12.1 L per kilogram of 4-(2-oxo-2,3-dihydrobenzimidazol-1-yl)butyric acid used in the Section A-1 reaction. In other such embodiments, the additional amount of solvent charged to the reactor for the Friedel-Crafts reaction (in addition to the solvent that is charged as part of the Section A-1 product mixture) is from about 0.53 to about 0.91 (or from about 0.60 to about 0.71) times the amount of solvent used in the Section A-1 reaction. In some such embodiments, for example, the additional amount is about 0.67 times the amount used in the Section A-1 reaction. In some embodiments when the chloro 2,3-dihydro-2-oxo-1H-benzimidazol-1-butanoate reagent is prepared in accordance with Section A-1, the Lewis acid in the Friedel-Crafts reaction is $AlCl_3$, and the total amount of solvent contained in the $AlCl_3$ slurry charged to the reactor is from about 3.7 to about 5.3 L (or from about 4.5 to about 5.1 L) per kilogram of 4-(2-oxo-2,3-dihydrobenzimidazol-1-yl)butyric acid used in the Section A-1 reaction. To illustrate, in some such embodiments, the amount of solvent is about 4.8 L per kilogram of 4-(2-oxo-2,3-dihydrobenzimidazol-1-yl)butyric acid used in the Section A-1 reaction. Although it is contemplated that solvent amounts outside the above ranges may be used, such amounts may coincide with production of undesirable byproducts.

The Friedel-Crafts reaction may be conducted over a wide range of temperatures. In some embodiments, Friedel-Crafts reaction is conducted at a temperature of greater than about 40° C. In some embodiments, the temperature is from about 45 to about 65° C. In some such embodiments, the temperature is from about 55 to about 62° C. In other such embodiments, the temperature is from about 50 to about 60° C. To illustrate, in some embodiments, the temperature is about 60° C. Although it is contemplated that lesser temperatures than the above ranges may be used, such temperatures may coincide with slower reaction rates and/or production of undesirable byproducts due to intermolecular side reactions. And, although it is contemplated that greater temperatures than the above ranges may be used, such temperatures may coincide with undesirable solvent loss, particularly when the solvent is dichloromethane.

In some embodiments, the temperature of the reaction mixture is decreased after the desired conversion has occurred. For example, in some such embodiments, the temperature is decreased to about 12° C.

The Friedel-Crafts reaction may be conducted over a wide range of pressures. In some embodiments, the pressure (absolute) is greater than atmospheric pressure. In some such embodiments, the pressure (absolute) is from about 2.0 to about 3.0 bar, or from about 2.6 to about 2.8 bar. To illustrate, in some embodiments, the pressure (absolute) is about 2.7 bar. Although it is contemplated that greater pressures than these ranges may be used, such pressures may require more costly equipment designed to effectively handle such pressures. And, although it is contemplated that lesser pressures than these ranges may be used, such pressures may coincide with undesirable solvent loss, particularly when the solvent is dichloromethane. Such pressures also may coincide with production of undesirable byproducts.

The reaction time for the Friedel-Crafts reaction may depend on various factors including, for example, the reaction temperature, characteristics of the solvent, relative amounts of the ingredients, and the desired conversion. In a batch reactor, the reaction time for the Friedel-Crafts reaction is generally at least about 1 minute, typically at least about 5 minutes, and more typically greater than about 1 hour. In some embodiments, for example, the reaction time for the Friedel-Crafts reaction is from about 2.5 to about 12 hours, or from about 2 to about 6 hours. To illustrate, in some embodiments, the reaction time is about 4 hours.

In some embodiments, the reaction time includes a period over which the chloro 2,3-dihydro-2-oxo-1H-benzimidazol-1-butanoate and Lewis acid are combined. In some embodiments, for example, the chloro 2,3-dihydro-2-oxo-1H-benzimidazol-1-butanoate is charged to a reactor containing the Lewis acid (e.g., $AlCl_3$) or vice versa over a period of from about 2 to about 10 hours. In some embodiments, this charge occurs over a period of from about 3 to about 6 hours. In other embodiments, the charge occurs over a period of from about 2 to about 5 hours. To illustrate, in some embodiments, the chloro 2,3-dihydro-2-oxo-1H-benzimidazol-1-butanoate is charged to a reactor containing the Lewis acid (e.g., $AlCl_3$) or vice versa over a period of about 4 hours. Although it is contemplated that charge times less than these ranges may be used, such charge times may coincide with production of undesirable byproducts due to intermolecular side reactions. And, although it is contemplated that charge times greater than these ranges may be used, such charge times may coincide with loss of throughput. When there is a charge period, the reaction mixture is typically subsequently maintained (or "aged") for an additional amount of time at, for example, the same conditions (e.g., temperature and/or pressure) while being agitated (e.g., stirred). In some embodiments, for example, this additional amount of time is from about 30 minutes to about 2 hours, or from about 45 to about 75 minutes. To illustrate, in some embodiments, the reaction mixture is maintained for an additional hour following the charge. Although it is contemplated that lesser aging periods than these ranges may be used, they may coincide with reduced conversion and yield. And, although it is contemplated that greater aging periods may be used, they may coincide with greater product decomposition and inefficient use of equipment and manpower.

To initiate the hydrolysis reaction, the slurry from the Friedel-Crafts reaction is added to acid or vice versa.

Although it is contemplated that various acids (or combinations thereof) may be used in the hydrolysis, the acid preferably is a strong acid. In some embodiments, for example, the acid is HCl.

The amount of acid charged to the reactor may vary. In general, it is preferable to use an excess of acid. In some embodiments, for example, the amount of acid (e.g., HCl) charged to the reactor is about 1.05 equivalents, based on moles of chloro 2,3-dihydro-2-oxo-1H-benzimidazol-1-butanoate. In some embodiments wherein the chloro 2,3-dihydro-2-oxo-1H-benzimidazol-1-butanoate is prepared in accordance with Section A-1, the amount of acid used in the hydrolysis is about 1.05 equivalents, based on the moles of 4-(2-oxo-2,3-dihydrobenzimidazol-1-yl)butyric acid used in the Section A-1 reaction.

In general, the acid preferably is prepared in the form of an aqueous solution before being combined with the other ingredients of the reaction. In some such embodiments, the mass ratio of HCl to water in the acid solution is from about 0.034 to about 0.142, or from about 0.038 to about 0.061. To illustrate, in some embodiments, the mass ratio is about 0.044 or about 0.045. Although it is contemplated that mass ratios that are less than the above ratios may be used, such ratios may coincide with a greater concentration of salt impurities in the product. And, although it is contemplated that mass ratios that are greater than the above ratios may be used, such ratios may coincide with yield loss.

The amount of water used for the hydrolysis reaction may vary. In some embodiments, for example, the total amount of water is from about 73 to about 245 equivalents (or from about 147 to about 196 equivalents), based on the amount of chloro 2,3-dihydro-2-oxo-1H-benzimidazol-1-butanoate used. In some embodiments wherein the chloro 2,3-dihydro-2-oxo-1H-benzimidazol-1-butanoate is prepared in accordance with Section A-1, the amount of water used in the hydrolysis is from about 73 to about 245 equivalents (or from about 147 to about 196 equivalents), based on the moles of 4-(2-oxo-2,3-dihydrobenzimidazol-1-yl)butyric acid used in the Section A-1 reaction. To illustrate, in some embodiments, the total amount of water used in the hydrolysis is about 171 equivalents, based on the moles of 4-(2-oxo-2,3-dihydrobenzimidazol-1-yl)butyric acid used in the Section A-1 reaction. Although it is contemplated that lesser amounts of water than the above ranges may be used, such amounts may coincide with a greater concentration of undesirable salt impurities in the final product.

The hydrolysis may be conducted over a wide range of temperatures. This reaction is exothermic, and, therefore, will generally increase the temperature of the reaction mixture as the reaction progresses. In some embodiments, the slurry from the Friedel-Crafts reaction is added (preferably over time, e.g., portion-wise) to an aqueous acid mixture (e.g., 33% HCl) that is at a temperature of about 0° C. at a rate that causes the temperature to be maintained at from about 0 to about 38° C., from about 0 to about 20° C., from about 10 to about 40° C., or from about 10 to about 15° C. To illustrate, in some embodiments, the aqueous acid mixture is charged at a rate that causes the temperature to be maintained at about 12° C. Once the charge is complete, the reaction mixture preferably is maintained at a temperature of from about 0 to about 65° C. until all (or essentially all) the solvent has been distilled off. In some embodiments, the temperature is from about 10 to about 40° C. In other embodiments, the temperature is from about 35 to about 50° C. To illustrate, in some embodiments, the temperature is about 38° C. Although it is contemplated that temperatures less than the above ranges may generally be used, such temperatures may coincide with ice formation and reduced or delayed hydrolysis. And, although it is contemplated that greater temperatures than the above ranges may generally be used, such temperatures may coincide with foaming, solvent loss (particularly when the solvent is dichloromethane), and/or product decomposition.

The hydrolysis may be conducted over a wide range of pressures. In some embodiments, the hydrolysis is conducted at a sub-atmospheric pressure. Such a sub-atmospheric pressure may be advantageous for both distilling off the solvent (e.g., dichloromethane) used in the Friedel-Crafts reaction and cooling of the strongly exothermic hydrolysis. This can increase throughput and decrease energy consumption. In some embodiments, the pressure (absolute) is from about 100 to about 1000 mbar, from about 200 to about 900 mbar, or from about 270 to about 470 mbar. In other embodiments, the pressure (absolute) is from about 300 mbar to about atmospheric pressure. To illustrate, in some embodiments, the pressure (absolute) is about 300 mbar. Such pressure ranges are particularly suitable for distilling off dichloromethane at from about 10 to about 40° C. In general, such pressure ranges may be used while the slurry from the Friedel-Crafts reaction is being transferred to the acid mixture (or vice versa), as well as during the remaining portion of the reaction. This allows the distillation of the solvent to occur in parallel to the transfer and reaction. In some embodiments, the pressure is increased during the hydrolysis. In some such embodiments, for example, the hydrolysis is initiated at a pressure (absolute) of about 300 mbar, and then allowed to increase up about atmospheric pressure. Although it is contemplated that pressures less than the above ranges may be used, such pressures may coincide with an undesirable rate of solvent loss, particularly when the solvent is dichloromethane.

The reaction time for the hydrolysis may depend on various factors including, for example, the reaction temperature, characteristics of the solvent, relative amounts of the ingredients, pressure, and dissolution of aluminum hydroxide formed during the hydrolysis. In some embodiments, the reaction conditions are maintained until distillation of the solvent from Friedel-Crafts reaction is essentially (or totally) complete.

In some embodiments, the distillate is recycled. Under the above reaction conditions, the distillate tends to comprise solvent as well as water (e.g., about 3% (vol/vol). When the solvent is non-polar (e.g., dichloromethane), the non-polar solvent and water in the distillate can be separated by, for example, pumping the distillate through a coalescer. Such a coalescer may be used to produce a non-polar solvent having a water content of no greater than, for example, about 0.2% (vol/vol). In some embodiments, additional water is removed using, for example, molecular sieves (e.g., 4 Å molecular sieves). The dried non-polar solvent may be reused in the process.

Both the Friedel-Crafts reaction and hydrolysis may be conducted under various atmospheres. In some embodiments, for example, both are conducted under inert atmospheres, which may be different, but, preferably are the same. One such atmosphere, for example, comprises $N_2$. In some such embodiments, the atmosphere consists of (or consists essentially of) $N_2$.

Both the Friedel-Crafts reaction and hydrolysis may be conducted with various reactor types. In some embodiments, for example, the reactor is a stirred-tank reactor. Glass and glass-lined reactors are often preferred, although any composition stable when exposed to the reaction mixture may be used. For example, during the hydrolysis, the reactor components in contact with the reaction mixture may comprise, for example, a stainless steel alloy (HASTELLOY®) that is resistant to degradation in acidic conditions. Because HCl gas is produced during the Friedel-Crafts reaction, the reactor used during the Friedel-Crafts reaction preferably comprises a mechanism to safely allow the HCl gas to be removed, such as, for example, a mechanism comprising an overpressure vent. Also, during the charging of the Lewis acid (e.g., $AlCl_3$) and the remaining later stages of the Friedel-Crafts reaction, the reaction mixture preferably is agitated (e.g., stirred) at a rate that is sufficiently fast to minimize intermolecular side reactions and production of undesirable byproducts, while also being sufficiently slow to minimize crusting of the Lewis acid on the reactor wall.

It is contemplated that the product of this hydrolysis may be used in the next step without further purification or isolation. In general, however, the product preferably is isolated and purified. This may be achieved by various separation and washing techniques. To illustrate, the temperature of the product mixture may be decreased to a temperature that precipitates a desired amount of the 8,9-dihydro-2H,7H-2,9a-diazabenzo[cd]azulene-1,6-dione product. In some embodiments, the temperature of the product mixture is adjusted to a temperature of from about −5 to about 20° C., from about −5 to about 5° C., or from about 0 to about 5° C. Although it is contemplated that temperatures less than these ranges may be used, such temperatures may coincide with a greater concentration of undesirable impurities in the product. And, although it is contemplated that temperatures greater than these ranges may be used, such temperatures may coincide with a yield loss.

Following the temperature adjustment, solid 8,9-dihydro-2H,7H-2,9a-diazabenzo[cd]azulene-1,6-dione may be separated from the aqueous mixture using various separation techniques, such as, for example, centrifugation. Afterward, the product preferably is washed using water one or more times. In some embodiments, for example, the product is washed with water 4 times. The amount of water used during a washing may vary. In some embodiments, for example, the amount of water used in a wash is from about 0.9 to about 1.8 kg (or from about 1.2 to about 1.7 kg) per kilogram of chloro 2,3-dihydro-2-oxo-1H-benzimidazol-1-butanoate reagent used. In some embodiments wherein the chloro 2,3-dihydro-2-oxo-1H-benzimidazol-1-butanoate is prepared in accordance with Section A-1, the amount of water used in a wash is from about 1 to about 2 kg (or from about 1.3 to about 1.8 kg) per kilogram of 4-(2-oxo-2,3-dihydrobenzimidazol-1-yl) butyric acid used in the Section A-1 reaction. To illustrate, in some embodiments, the amount of water used in a wash is about 1.5 kg per kilogram of 4-(2-oxo-2,3-dihydrobenzimidazol-1-yl) butyric acid used in the Section A-1 reaction. Although it is contemplated that lesser amounts of water than the above ranges may be used, such amounts may coincide with a greater concentration of salt impurities remaining in the product. And, although it is contemplated that greater amounts of water may be used than the above ranges, such amounts may coincide with yield loss.

In some embodiments, the product also is washed with one or more organic solvents. In some such embodiments, the product is washed with acetone one or more times. In other embodiments, the product is washed with isopropanol one or more times. In some such embodiments, for example, the product is washed with isopropanol one time. The amount of isopropanol used during a wash may vary. In some embodiments, for example, the amount of isopropanol used in a wash is from about 0.9 to about 4.2 kg (or from about 1.4 to about 1.7 kg) per kilogram of chloro 2,3-dihydro-2-oxo-1H-benzimidazol-1-butanoate reagent used. In some embodiments wherein the chloro 2,3-dihydro-2-oxo-1H-benzimidazol-1-butanoate is prepared in accordance with Section A-1, the amount of isopropanol used in a wash is from about 1.0 to about 4.5 kg (or from about 1.5 to about 1.8 kg) per kilogram of 4-(2-oxo-2,3-dihydrobenzimidazol-1-yl)butyric acid used in the Section A-1 reaction. To illustrate, in some embodiments, the amount of isopropanol used in a wash is about 1.6 kg per kilogram of 4-(2-oxo-2,3-dihydrobenzimidazol-1-yl) butyric acid used in the Section A-1 reaction. Although it is contemplated that lesser amounts of isopropanol than the above ranges may be used, such amounts may coincide with greater concentrations of organic impurities remaining in the product. And, although it is contemplated that greater amounts of isopropanol may be used than the above ranges, such amounts may coincide with yield loss.

Each washing of the product with organic solvent (e.g., isopropanol) preferably is conducted at a temperature of from about −5 to about 20° C., from about 0 to about 10° C., or from about 0 to about 5° C. Although it is contemplated that temperatures less than these ranges may be used, such temperatures may coincide with a greater concentration of impurities remaining in the product. And, although it is contemplated that greater temperatures than these ranges may be used, such temperatures may coincide with yield loss.

Drying of the washed product (particularly complete drying) generally is not necessary before use of the product in the next step. Thus, in at least some embodiments, the washed product is not dried before its use in the next step. This provides, for example, savings in energy and time.

In some embodiments wherein aluminum chloride is used as the Lewis acid in the Friedel-Crafts reaction, aluminum hydroxide is recovered from the aqueous supernatant that is produced when the solid 8,9-dihydro-2H,7H-2,9a-diazabenzo[cd]azulene-1,6-dione product is separated from the reaction product mixture. In such embodiments, the aqueous supernatant may, for example, be treated with a base (typically a strong base, such as sodium hydroxide) and carbon dioxide. This causes aluminum hydroxide to precipitate, which, in turn, can be recovered using various separation techniques, such as, for example, centrifugation. Use of the chlorinating agents discussed above in Section A-1 (particularly oxalyl chloride) rather than, for example, $PCl_5$, in the Friedel-Crafts reaction tends to be particularly beneficial in embodiments wherein aluminum hydroxide is recovered. $PCl_5$, in contrast, tends to produce phosphorus impurities that can make the aluminum hydroxide less viable for other uses.

A-3. Preparation of 4,5-dihydro-imizidazo[4,5,1-jk] [1]benzazepin-2,6,7[1H]-trione-6-oxime In some embodiments, the synthesis of zilpaterol or a salt thereof begins by or includes preparing 4,5-dihydro-imidazo [4,5,1-jk][1]benzazepin-2,6,7[1H]-trione-6-oxime:

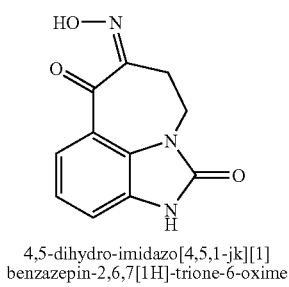 [SMILES: O=C1/C(=N\O)CCn2c(=O)[nH]c3cccc1c32]

4,5-dihydro-imidazo[4,5,1-jk][1]
benzazepin-2,6,7[1H]-trione-6-oxime

In some embodiments, the 4,5-dihydro-imidazo[4,5,1-jk][1] benzazepin-2,6,7[1H]-trione-6-oxime is prepared by, for example, reacting 8,9-dihydro-2H,7H-2,9a-diazabenzo[cd] azulene-1,6-dione with an inorganic nitrite via the following oximation reaction:

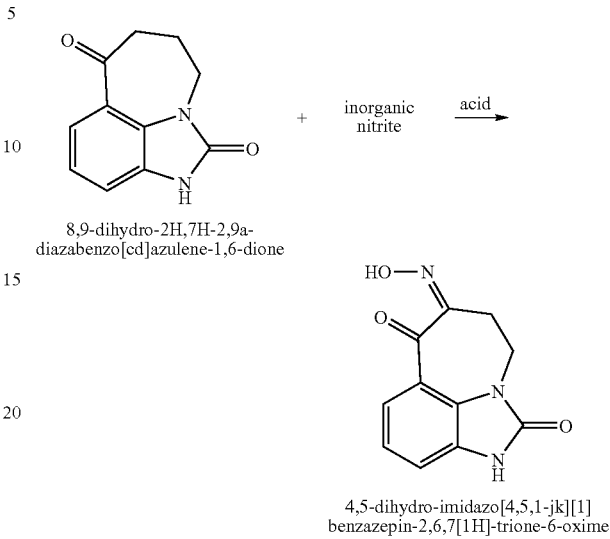

8,9-dihydro-2H,7H-2,9a-
diazabenzo[cd]azulene-1,6-dione 4,5-dihydro-imidazo[4,5,1-jk][1]
benzazepin-2,6,7[1H]-trione-6-oxime The 8,9-dihydro-2H,7H-2,9a-diazabenzo[cd]azulene-1,6-dione used in the above reaction may be obtained from a commercial vendor (to the extent any exist), prepared using a process discussed above in Section A-2, or prepared using a different process. In some embodiments, the 8,9-dihydro-2H, 7H-2,9a-diazabenzo[cd]azulene-1,6-dione is prepared by a process described in U.S. Pat. No. 4,585,770. In some preferred embodiments, the 8,9-dihydro-2H,71-1-2,9a-diazabenzo[cd]azulene-1,6-dione is prepared using a process discussed above in Section A-2.

The inorganic nitrite may vary. In some embodiments, the inorganic nitrite comprises nitrosyl sulfate:

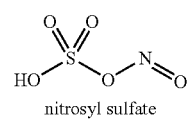

nitrosyl sulfate

In other embodiments, the inorganic nitrite comprises at least one nitrite salt. Such a nitrite salt may be selected from various salts. In some embodiments, the nitrite salt comprises sodium nitrite ("$NaNO_2$").

The amount of inorganic nitrite may vary. In some embodiments, for example, the amount is from about 1.10 to about 1.26 equivalents. In some such embodiments, the amount is from about 1.16 to about 1.26 equivalents (or from about 1.20 to about 1.22 equivalents), based on the moles of 8,9-dihydro-2H,7H-2,9a-diazabenzo[cd]azulene-1,6-dione reagent. In other embodiments, the amount is from about 1.10 to about 1.20 equivalents, based on the moles of 8,9-dihydro-2H,7H-2,9a-diazabenzo[cd]azulene-1,6-dione reagent. Although it is contemplated that lesser amounts than these ranges may be used, such amounts may coincide with reduced conversion. And, although it is contemplated that greater amounts than these ranges may be used, such amounts may coincide with production of undesirable byproducts.

The acid may be selected from various acids. In some embodiments, the acid comprises a strong acid. Preferred acids include HCl. The amount of acid may vary. In general, an excess of acid is used, relative to the amount of 8,9-dihydro-2H,7H-2,9a-diazabenzo[cd]azulene-1,6-dione reagent. In some embodiments, for example, the amount is from about 1.24 to about 1.75 equivalents (or from about 1.52 to about 1.68 equivalents), based on the moles of 8,9-dihydro-2H-7H-2,9a-diazabenzo[cd]azulene-1,6-dione reagent. To illustrate, in some embodiments, the amount is about 1.60 equivalents. Although it is contemplated that lesser amounts of acid than these ranges may be used, such amounts may coincide with reduced conversion. And, although it is contemplated that greater amounts than these ranges may be used, such amounts may coincide with a greater concentration of impurities in the product. Greater acid concentrations also may coincide with reactor corrosion, depending on the composition of the reactor.

This reaction typically is conducted in the presence of one or more solvents. In some embodiments, the solvent comprises dimethylformamide. In some embodiments, the amount of solvent is from about 15.5 to about 25.6 L (or from about 17.4 to about 21.0 L, or from about 18.2 to about 18.3 L) per kilogram of 8,9-dihydro-2H,7H-2,9a-diazabenzo[cd]azulene-1,6-dione reagent. Although it is contemplated that smaller amounts than the above ranges may be used, such amounts may coincide with reduced dissolution and/or production of undesirable byproducts. And, although it is contemplated that greater amounts than the above ranges may be used, such amounts may coincide with yield loss.

In some embodiments, this reaction is initiated by first combining the solvent (e.g., dimethylformamide), inorganic nitrite (e.g., $NaNO_2$), and 8,9-dihydro-2H,7H-2,9a-diazabenzo[cd]azulene-1,6-dione. In some embodiments, this is carried out at a temperature of from about 40 to about 65° C., or from about 40 to about 50° C. To illustrate, in some embodiments, this is carried out at a temperature of about 45° C. Although it is contemplated that lesser temperatures than the above ranges may be used, such temperatures may coincide with reduced dissolution and/or production of undesirable byproducts. And, although it is contemplated that greater temperatures than the above ranges may be used, such temperatures may coincide with decomposition of the 8,9-dihydro-2H,7H-2,9a-diazabenzo[cd]azulene-1,6-dione reagent.

In some embodiments, the resulting mixture is pre-heated before the acid addition. In some such embodiments, for example, the mixture is pre-heated to from about 47 to about 63° C., or from about 48 to about 55° C. To illustrate, in some embodiments, the mixture is pre-heated to about 50° C. Although it is contemplated that lesser temperatures than the above ranges may be used, such temperatures may coincide with reduced conversion. And, although it is contemplated that greater temperatures than the above ranges may be used, such temperatures may coincide with production of undesirable byproducts.

After pre-heating, the acid (e.g., HCl) is charged to the reactor. In some embodiments, the charged acid is in the form of an aqueous solution. When, for example, the acid is HCl, the HCl concentration in the solution is typically not greater than about 50%, not greater than about 48%, from about 1 to about 40%, or from about 32 to about 33% (mass/vol). Gaseous HCl (100%) may, for example, be used as well.

The total reaction time for this reaction may depend on various factors including, for example, the reaction temperature, characteristics of the solvent, relative amounts of the ingredients, and the desired conversion.

The reaction time typically includes an extended period over which the acid solution is combined with the rest of the reaction components. In some such embodiments, for example, the acid is charged over a period of from about 10 minutes to about 2 hours, from about 30 minutes to about 1 hour, or from about 30 to about 45 minutes. Although it is contemplated that shorter time periods than the above ranges may be used, such time periods may coincide with too great of an increase in the temperature (the reaction is exothermic) and production of undesirable byproducts. Although it is contemplated that greater time periods than the above ranges may be used, such periods may coincide with reduced conversion, as well as inefficient use of equipment and manpower.

As discussed above, the temperature typically increases during the charging of the acid due to the exothermic nature of the reaction. In some embodiments, the temperature increases to a temperature of from about 54 to about 73° C., from about 55 to about 70° C., from about 60 to about 70° C., or from about 60 to about 66° C. To illustrate, in some embodiments, the temperature increases to about 63° C. Although it is contemplated that lesser temperature increases than the above ranges may be suitable, such temperatures may coincide with reduced conversion. And, although it is contemplated that greater temperature increases than the above ranges may be suitable, such temperatures may coincide with production of undesirable byproducts.

Once the acid has been charged, the reaction mixture is further maintained (or "aged"), typically while being agitated (e.g., stirred), for an additional period. In some embodiments, the additional period is from about 15 minutes to about 21 hours, from about 15 minutes to about 10 hours, from about 15 minutes to about 2 hours, or from about 25 to about 40 minutes. To illustrate, in some embodiments, the additional period is about 30 minutes. Although it is contemplated that shorter time periods than the above ranges may be used, such time periods may coincide with reduced conversion. And, although it is contemplated that greater time periods than the above ranges may be used, such periods may coincide with production of undesirable byproducts, as well as inefficient use of equipment and manpower.

The reaction conditions (e.g., temperature, pressure, and/or stirring rate) during the aging period may be maintained at the same conditions as during the acid addition. The conditions, however, also may be different. In some embodiments, the temperature during this additional period is from about 55 to about 70° C., from about 55 to about 65° C., or from about 58 to about 62° C. To illustrate, in some embodiments, the temperature is about 60° C. Although it is contemplated that lesser temperatures than the above ranges may be used, such temperatures may coincide with reduced conversion. And, although it is contemplated that greater temperatures than the above ranges may be used, such temperatures may coincide with production of undesirable byproducts.

In some embodiments, water is charged to the reactor following the aging period. In some embodiments, the temperature of the reaction mixture is adjusted before the water addition to temperature of from about 0 to about 48° C., from about 35 to about 40° C., or from about 35 to about 38° C. Although it is contemplated that lesser temperatures than these ranges may be used, such temperatures may coincide with difficulties in filtration of the product and yield loss. And, although it is contemplated that greater temperatures than these ranges may be used, such temperatures may coincide with production of undesirable byproducts. In some embodiments, the temperature adjustment before the water addition is carried out over an extended period of time. In some such embodiments, for example, the temperature is adjusted over a period of from about 30 minutes to about 5 days, from about 1 to about 10 hours, from about 3 to about 5 hours, or from about 2 to about 4 hours. Although it is contemplated that shorter time periods than these ranges may be used, such time periods may coincide with difficulties in filtration of the product. And, although it is contemplated that greater time periods than these ranges may be used, such temperatures may coincide with production of undesirable byproducts. In general, the adjusted temperature is maintained during at least a portion (or essentially all) of the water addition.

In some embodiments, the addition of water occurs over an extended time period. For example, in some embodiments, the water is added over a period of from about 30 minutes to about 5 hours, from about 1 to about 4 hours, or from about 2 to about 3 hours. Although it is contemplated that shorter time periods than these ranges may be used, such time periods may coincide with difficulties in filtration of the product and yield loss. And, although it is contemplated that greater time periods than these ranges may be used, such temperatures may coincide with a greater concentration of impurities in the product.

The amount of water may vary. In some embodiments, for example, the amount is from about 33 to about 88 equivalents (or from about 45 to about 67 equivalents, or from about 54 to about 55 equivalents), based on the moles of 8,9-dihydro-2H, 7H-2,9a-diazabenzo[cd]azulene-1,6-dione reagent. Although it is contemplated that amounts outside these ranges may be used, such amounts may coincide with a greater concentration of impurities in the product and yield loss.

In some embodiments, the temperature of the reaction mixture is adjusted to promote precipitation of the product. In embodiments where water is added, this temperature adjustment generally occurs after the water addition. In some such embodiments, for example, the temperature is decreased to a temperature of from about −10 to about 10° C., from about −5 to about 2° C., or from about −2 to about 0° C. Although it is contemplated that lesser temperatures than these ranges may be used, such temperatures may coincide with formation of ice and/or a greater concentration of impurities in the product. And, although it is contemplated that greater temperatures than these ranges may be used, such temperatures may coincide with less crystallization and yield loss. In some embodiments, the temperature adjustment is carried out over an extended period of time. In some such embodiments, for example, the temperature is adjusted over a period of from about 1 to about 10 hours, from about 2 to about 6 hours, from about 2 to about 5 hours, or from about 2 to about 4 hours. Although it is contemplated that shorter time periods than these ranges may be used, such time periods may coincide with less crystallization and yield loss.

In some embodiments, once the temperature has been adjusted to promote product precipitation, the temperature is maintained within the above ranges for a period of time. In some such embodiments, the temperature is maintained within such ranges for a period of not greater than about 14 days, from about 1 to about 40 hours, from about 30 minutes to about 2 hours, or from about 45 minutes to about 2 hours. Although it is contemplated that shorter time periods than these ranges may be used, such time periods may coincide with less crystallization and yield loss.

This reaction may be conducted under various atmospheres, but preferably is conducted under an inert atmosphere. One such atmosphere, for example, comprises $N_2$.

This reaction may be conducted over a wide range of pressures, including atmospheric pressure (absolute), less than atmospheric pressure (absolute), and greater than atmospheric pressure (absolute). It is typically preferred, however, to conduct the reaction at about atmospheric pressure (absolute).

This reaction may be conducted with various reactor types. In some embodiments, for example, the reactor is a stirred-tank reactor. Glass and glass-lined reactors are often preferred, although any composition stable when exposed to the reaction mixture may be used.

It is contemplated that the product mixture may subsequently be used as a reagent without further isolation or purification. Normally, however, the 4,5-dihydro-imidazo[4, 5,1-jk][1]benzazepin-2,6,7[1H]-trione-6-oxime product is first separated from the product mixture, and then purified. In some embodiments, this is achieved using, for example, various methods known in the art.

In some embodiments, solid 4,5-dihydro-imidazo[4,5,1-jk][1]benzazepin-2,6,7[1H]-trione-6-oxime in the product mixture is separated from the mixture using, for example, filtration.

In some embodiments, the solvent (e.g., dimethylformamide) is recycled from the mother liquor by rectification. In embodiments wherein the mother liquor comprises both water and dimethylformamide, for example, the water may be removed, followed by distillation of dimethylformamide.

Following separation, the product preferably is washed using water one or more times. In some embodiments, for example, the product is washed with water 2, 3, or 4 times. The amount of water used during a washing may vary. In some embodiments, for example, the total amount of water used during the washings is from about 4.4 to about 9.0 L (or from about 5.4 to about 7.5 L) per kilogram of 8,9-dihydro-2H,7H-2,9a-diazabenzo[cd]azulene-1,6-dione reagent used in the synthesis. In some embodiments, for example, the total amount of water is about 6.0 L per kilogram of 8,9-dihydro-2H,7H-2,9a-diazabenzo[cd]azulene-1,6-dione reagent used in the synthesis. Although it is contemplated that lesser amounts of water than the above ranges may be used, such amounts may coincide with a greater concentration of impurities remaining in the product. And, although it is contemplated that greater amounts of water may be used than the above ranges, such amounts may coincide with yield loss. Separation of the water from the product may be achieved using, for example, centrifugation.

In some embodiments, the product also is washed with one or more organic solvents. In some such embodiments, the product is washed with acetone one or more times. In some such embodiments, for example, the product is washed with acetone one time. The amount of acetone used during a wash may vary. In some embodiments, for example, the total amount of acetone is from about 2.2 to about 8.6 L (or from about 2.8 to about 4.4 L) per kilogram of 8,9-dihydro-2H,7H-2,9a-diazabenzo[cd]azulene-1,6-dione reagent used in the synthesis. In some embodiments, for example, the total amount of acetone is about 3.2 L per kilogram of 8,9-dihydro-2H,7H-2,9a-diazabenzo[cd]azulene-1,6-dione reagent used in the synthesis. Although it is contemplated that lesser amounts of acetone than the above ranges may be used, such amounts may coincide with greater concentrations of impurities and water remaining in the product. And, although it is contemplated that greater amounts of acetone may be used than the above ranges, such amounts may coincide with yield loss. Separation of the acetone from the product may be achieved using, for example, centrifugation.

In some embodiments, the washed 4,5-dihydro-imidazo[4, 5,1-jk][1]benzazepin-2,6,7[1H]-trione-6-oxime product is dried. In some embodiments, this is achieved by heating the solid at a temperature of from about 20 to about 80° C., or from about 20 to about 75° C. To illustrate, in some Such embodiments, the product is heated to a temperature of 65° C. Although it is contemplated that lesser temperatures than the above ranges may be used, such temperatures may coincide with loss of throughput. And, although it is contemplated that greater temperatures may be used than the above ranges, such amounts may coincide with product decomposition. In some embodiments, the heating is maintained for less than about 3 days, or from about 5 to about 10 hours. Although it is contemplated that drying periods longer than the above ranges may be used, such longer periods may coincide with loss of throughput, as well as inefficient use of equipment and manpower. In some embodiments, this drying occurs under vacuum.

A-4. Preparation of Zilpaterol

Zilpaterol may be prepared from any of the products from Sections A-1, A-2, or A-3 using various processes.

For example, the product of Section A-3 can be used to produce zilpaterol by directly using it as a reagent in the process illustrated by Example 5 below. The product of Section A-2 can be used to make zilpaterol by, for example, using it as a reagent to make the product of Section A-3 according to Section A-3, followed by using the product of Section A-3 as a reagent in the process illustrated by Example 5. And the product of Section A-1 can be used to make zilpaterol by, for example, using it as a reagent to make the product of Section A-2 according to Section A-2, followed by using the product of Section A-2 to make the product of Section A-3 according to Section A-3, followed by using the product of Section A-3 as a reagent in the process illustrated by Example 5. Such processes are further illustrated below in the example generic schemes in Section A-5.

Zilpaterol also may be made from the products of Sections A-1, A-2, and A-3 by, for example, combining the teachings of this patent with other processes known in the art. To illustrate, the product of Section A-3 can be used as a reagent to produce zilpaterol with the synthesis techniques discussed in, for example, U.S. Pat. No. 4,585,770. The product of Section A-2 can be used to make zilpaterol by, for example, using it as a reagent to make the product of Section A-3 according to Section A-3, followed using the product of Section A-3 as a reagent with the synthesis techniques discussed in, for example, U.S. Pat. No. 4,585,770. And the product of Section A-1 can be used to make zilpaterol by, for example, using it as a reagent to make the product of Section A-2 according to Section A-2, followed by using the product of Section A-2 as a reagent to make the product of Section A-3 according to Section A-3, followed by using the product of Section A-3 as a reagent with the synthesis techniques discussed in, for example, U.S. Pat. No. 4,585,770. See, e.g., U.S. Pat. No. 4,585,770 col. 2, line 33 to col. 4, line 2; col. 7, lines 51-68; and col. 11, lines 41-48 (discussing and exemplifying the preparation of a hydroxyamine compound from 4,5-dihydro-imidazo[4,5,1-jk][1]benzazepin-2,6,7[1H]-trione-6-oxime, and then the preparation of zilpaterol-HCl from the hydroxyamine compound).

A-5. Examples of Contemplated Reaction Schemes

This invention contemplates any processes that use any of the above reactions. In some embodiments, the process will comprise only one of the above reactions. In other embodiments, the process will comprise more than one of the above reactions. The following Scheme I generically illustrates a scenario wherein all the above reactions are used:

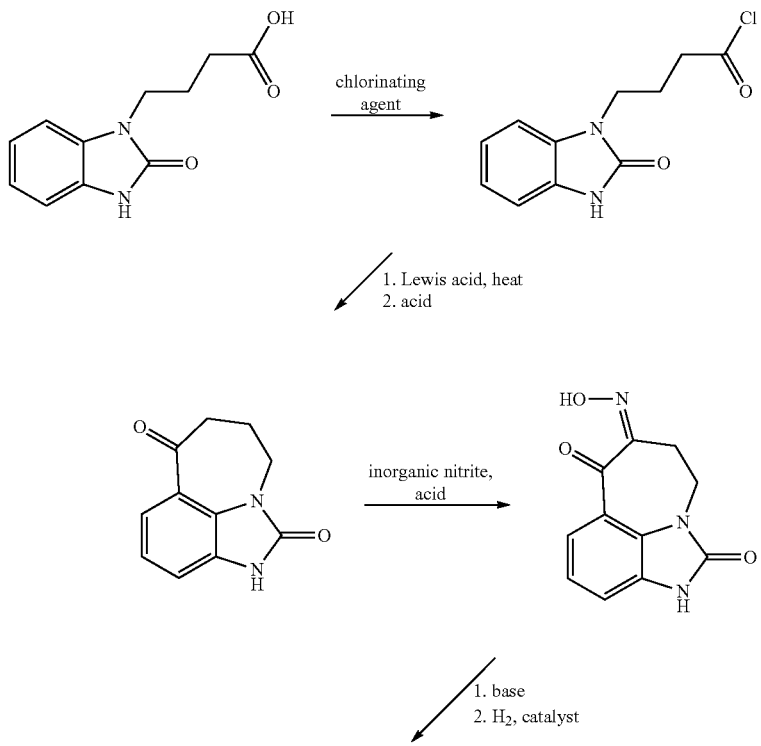

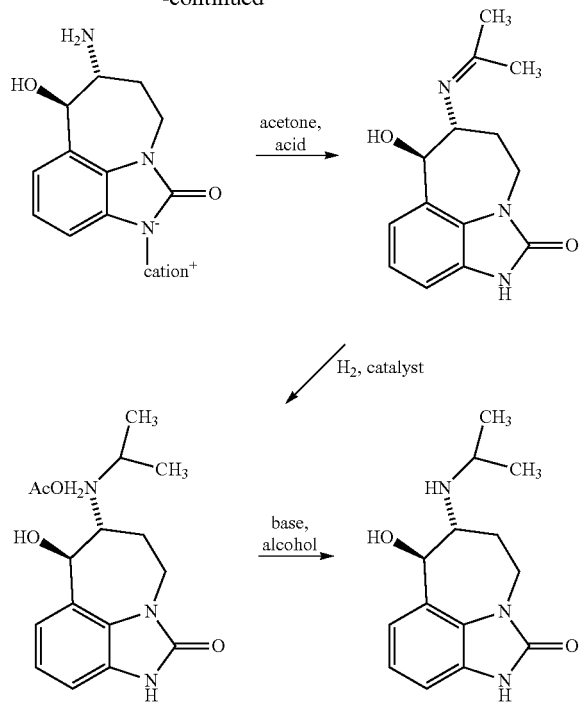

The following Scheme II generically illustrates the above scenario wherein the chlorinating agent comprises oxalyl chloride; the Lewis acid comprises AlCl$_3$; the hydrolysis acid following the Friedel-Crafts reaction comprises HCl; the inorganic nitrite comprises NaNO$_2$; the acid used in the oximation comprises HCl; water is added to the oximation product mixture to foster isolation of the oxime product; the base used to form the oxime salt comprises KOH; the catalyst for the first hydrogenation comprises palladium on carbon; the acid used in the formation of the isopropylideneamino compound comprises acetic acid; the catalyst for the second hydrogenation comprises platinum on carbon; and the base and alcohol used to form the zilpaterol free base comprise NaOH and ethanol, respectively:

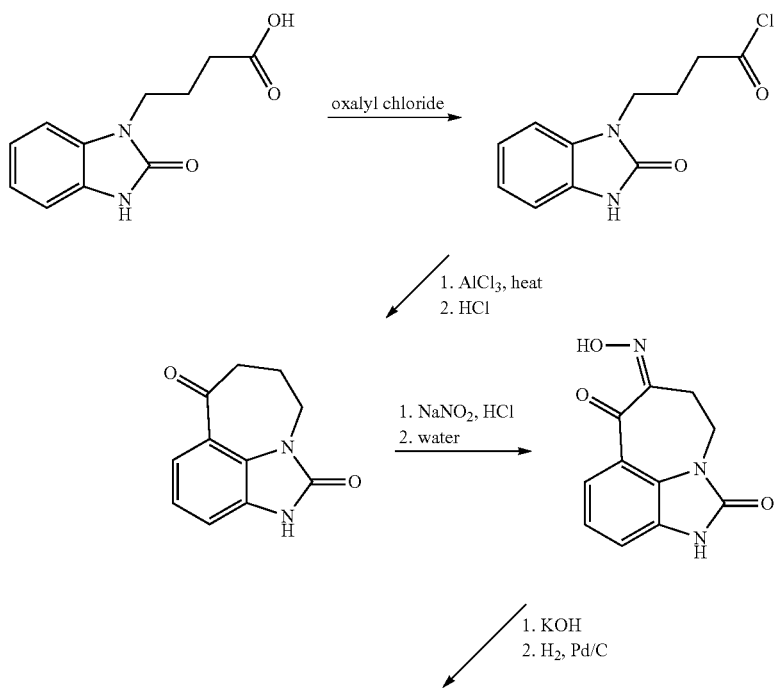

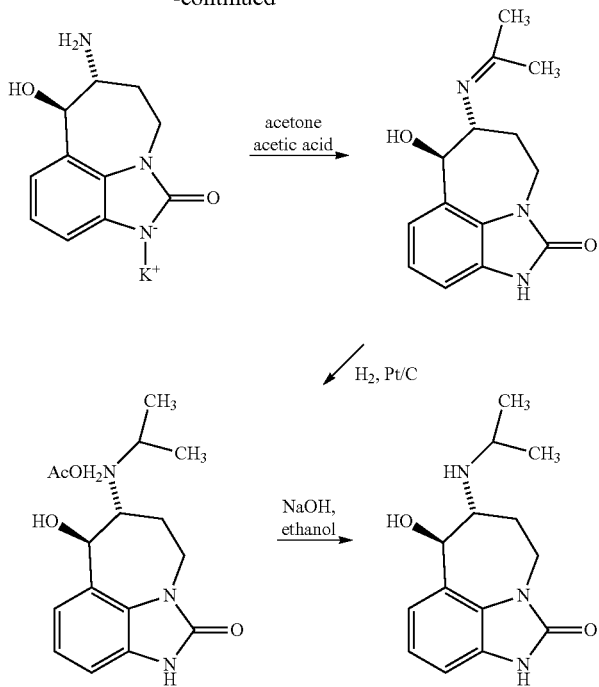

B. Salts

It should be recognized that this invention further encompasses embodiments wherein one or more of the reagents and/or products in the above synthesis reactions may be in the form of a salt. This is particularly true for the zilpaterol product, which may, for example, be in the form of one or more acid addition salts, such as an HCl salt. Salts may be, for example, base or acid addition salts. In general, an acid addition salt can be prepared using various inorganic or organic acids, and a base addition salt can be prepared using various inorganic or organic bases. Such salts can typically be formed by, for example, mixing a free base compound with an acid or mixing a free acid compound with a base using, for example, various methods known in the art. A salt may be advantageous due to one or more of its chemical or physical properties, such as stability in differing temperatures and humidities, or a desirable solubility in water, oil, or other solvent. In some instances, a salt of a compound also may be used as an aid in the isolation or purification of the compound. In some embodiments (particularly where the salt is intended for administration to an animal, or is a reagent for use in making a compound or salt intended for administration to an animal), the salt is pharmaceutically acceptable. The term "pharmaceutically acceptable" is used to characterize the salt as being appropriate for use in a pharmaceutical product. In general, a pharmaceutically acceptable salt has one or more benefits that outweigh any deleterious effect that the salt may have.

Examples of inorganic acids that typically may be used to form acid addition salts include hydrochloric, hydrobromic, hydroiodic, nitric, carbonic, sulfuric, and phosphoric acid. Examples of organic acids include, for example, aliphatic, cycloaliphatic, aromatic, araliphatic, heterocyclic, carboxylic, and sulfonic classes of organic acids. Specific examples of organic salts include cholate, sorbate, laurate, acetate, trifluoroacetate, formate, propionate, succinate, glycolate, gluconate, digluconate, lactate, malate, tartaric acid (and derivatives thereof, e.g., dibenzoyltartrate), citrate, ascorbate, glucuronate, maleate, fumarate, pyruvate, aspartate, glutamate, benzoate, anthranilic acid, mesylate, stearate, salicylate, p-hydroxybenzoate, phenylacetate, mandelate (and derivatives thereof), embonate (pamoate), ethanesulfonate, benzenesulfonate, pantothenate, 2-hydroxyethanesulfonate, sulfanilate, cyclohexylaminosulfonate, algenic acid, β-hydroxybutyric acid, galactarate, galacturonate, adipate, alginate, butyrate, camphorate, camphorsulfonate, cyclopentanepropionate, dodecylsulfate, glycoheptanoate, glycerophosphate, heptanoate, hexanoate, nicotinate, 2-naphthalesulfonate, oxalate, palmoate, pectinate, 3-phenylpropionate, picrate, pivalate, thiocyanate, tosylate, and undecanoate.

Examples of base addition salts may include, for example, metallic salts and organic salts. Metallic salts, for example, include alkali metal (group Ia) salts, alkaline earth metal (group IIa) salts, and other physiologically acceptable metal salts. Such salts may be made from aluminum, calcium, lithium, magnesium, potassium, sodium, and zinc. For example, a free acid compound may be mixed with NaOH to form such a base addition salt. Organic salts may be made from amines, such as trimethylamine, diethylamine, N,N'-dibenzylethylenediamine, chloroprocaine, ethanolamine, diethanolamine, ethylenediamine, meglumine (N-methylglucamine), and procaine. Basic nitrogen-containing groups may be quaternized with agents such as $C_1$-$C_6$-alkyl halides (e.g., methyl, ethyl, propyl, and butyl chlorides, bromides, and iodides), dialkyl sulfates (e.g., dimethyl, diethyl, dibuytl, and diamyl sulfates), long chain halides (e.g., decyl, lauryl, myristyl, and stearyl chlorides, bromides, and iodides), arylalkyl halides (e.g., benzyl and phenethyl bromides), and others.

C. Uses of Zilpaterol and Salts Thereof Prepared in Accordance with this Invention Compositions containing zilpaterol or a salt prepared in accordance with this invention may generally be used, for example, to increase the rate of weight gain, improve feed efficiency, and/or increase carcass leanness in livestock, poultry, and/or fish.

Typically, the zilpaterol or salt composition is administered orally. In some embodiments, the composition is added to the intended recipient animal's drinking water. In other embodiments, the zilpaterol or salt is added to the intended recipient's feed, either directly or as part of a premix. Suitable oral dosage forms include, for example, solid dosage forms (e.g., tablets, hard or soft capsules, granules, powders, etc.), pastes, and liquid dosage forms (e.g., solutions, suspensions, emulsions, syrups, etc.). These dosage forms optionally comprise one or more suitable excipients. Such excipients generally include, for example, sweetening agents, flavoring agents, coloring agents, preservative agents, inert diluents (e.g., calcium carbonate, sodium carbonate, lactose, calcium phosphate, sodium phosphate, or kaolin), granulating and disintegrating agents (e.g., corn starch or alginic acid), binding agents (e.g., gelatin, acacia, or carboxymethyl cellulose), and lubricating agents (e.g., magnesium stearate, stearic acid, or talc). Liquid compositions will generally comprise a solvent. The solvent preferably has sufficient chemical properties and quantity to keep the zilpaterol or salt solubilized at temperatures at the normal storage temperature for the composition. In some instances, it may be desirable for the compositions to comprise one or more preservatives. The presence of a preservative may, for example, allow for the compositions to be stored over a greater amount of time.

In some embodiments, the zilpaterol or salt is in the form of particles adhered to a support, which, in turn, is fed to the intended recipient animal. The supported zilpaterol or salt may be incorporated into the intended recipient's feed, either directly or as part of a premix. Contemplated supports include, for example, insert supports, such as calcium carbonate, limestone, oyster shell flour, talc, soybean hulls, soybean meal, soybean feed, soybean mill run, wheat middlings, rice hulls, corn meal, corn germ meal, corn gluten, starch, sucrose, and lactose. Particularly contemplated supports include corn cob supports, such as the support discussed in U.S. Pat. No. 5,731,028. In some embodiments employing a corn cob support, the size of the support is from about 300 to about 800 μm. Preferably, the zilpaterol or salt particles that are adhered to the support have a particle size that is less than the size of the support. Thus, for example, in some embodiments in which the support is from about 300 to about 800 μm, the particles (or at least about 95% of the particles) are less than about 250 μm. In some embodiments, the size of the majority of the particles is from about 50 to about 200 μm. To avoid generating dust when making the supported zilpaterol or salt, it is preferred to avoid using extremely small zilpaterol or salt particles. In some embodiments, for example, the zilpaterol or salt particle size distribution is such that less than about 5% of the zilpaterol or salt particles have a particle size of less than about 15 μm. The methods discussed in, for example, U.S. Pat. No. 5,731,028 (incorporated by reference into this patent) for making a specific size distribution of crystalline zilpaterol may generally be applied when making crystals having the above-described size distributions.

To the extent the composition is incorporated into feed, the feed mixture will vary depending on, for example, the type (e.g., species and breed), age, weight, activity, and condition of the intended recipient. For bovine and swine, various feeds are well known in the art, and often comprise cereals; sugars; grains; arachidic, tournsole, and soybean press cake; flours of animal origin, such as fish flour; amino acids; mineral salts; vitamins; antioxidants; etc. In general, the zilpaterol or salt composition can be incorporated into any feed that is available and used for the intended recipient animal.

It is contemplated that the zilpaterol or salt composition may be administered via non-oral routes, such as rectally, via inhalation (e.g., via a mist or aerosol), transdermally (e.g., via a transdermal patch), or parenterally (e.g., subcutaneous injection, intravenous injection, intramuscular injection, implanted device, partially implanted device etc.). In some particular embodiments, the composition is administered via an implant, such as a subcutaneous implant. For administration to bovine or swine animals, for example, the composition may be administered in the form of an implant behind the ear.

In general, the zilpaterol or salt composition is administered in a dosage form that provides an effective amount of the zilpaterol or salt. This is particularly true where the zilpaterol or salt is the only active ingredient in the composition. To the extent the zilpaterol or salt is administered with another active ingredient(s), the dosage preferably comprises an amount of the zilpaterol or salt that, together with the amount of other active ingredient(s), constitutes an effective amount. In the context of the zilpaterol or salt, an "effective amount" is an amount sufficient to increase the rate of weight gain, improve feed efficiency, and/or increase carcass leanness in the intended recipient (typically livestock, poultry, and/or fish).

When the composition is orally administered, it is typically preferred to use a daily dosage form. The preferred total daily dose of the zilpaterol or salt is typically greater than about 0.01 mg/kg (i.e., milligram of zilpaterol or salt per kilogram body weight), particularly for bovine and swine animals. In some such embodiments, the daily dose is from about 0.01 to about 50 mg/kg, from about 0.01 to about 10 mg/kg, from about 0.05 to about 2 mg/kg, from about 0.1 to about 1, or from about 0.1 to about 0.2 mg/kg. To illustrate, in some embodiments, the dose is about 0.15 mg/kg.

In some embodiments where the zilpaterol or salt is administered in the recipient animal's feed, the concentration of the zilpaterol or salt in the feed (on a 90% dry matter basis) is at least about 0.01 ppm (by weight). For bovine animals, the zilpaterol or salt concentration is preferably no greater than about 75 ppm (by weight). In some embodiments, for example, the zilpaterol or salt concentration is no greater than about 38 ppm, from about 0.5 to about 20 ppm, from about 3 to about 8 ppm, or from about 3.7 to about 7.5 ppm (by weight). For swine animals, the zilpaterol or salt concentration is preferably no greater than about 45 ppm (by weight). In some such embodiments, for example, the concentration is no greater than about 23 ppm, from about 0.5 to about 20 ppm, from about 2 to about 5 ppm, or from about 2.2 to about 4.5 ppm (by weight).

Although single oral daily doses are typically preferred, it is contemplated that shorter or longer periods between doses can be used, depending on, for example, the recipient's metabolism of the zilpaterol or salt. It is contemplated that smaller doses may be administered two or more times per day to achieve the desired total daily dose. Such multiple doses per day may, in some instances, be used to increase the total oral daily dose, if desired.

When administered via a subcutaneous implant, the preferred total daily dose of the zilpaterol or salt is typically greater than about 0.05 mg/kg (i.e., milligram of zilpaterol or salt per kilogram body weight), particularly for bovine and swine animals. In some embodiments, the daily dose is from about 0.1 to about 0.25 mg/kg.

If the zilpaterol or salt composition is administered parenterally via an injection, the concentration of the zilpaterol or salt in the dosage form preferably is sufficient to provide the desired therapeutically effective amount of the zilpaterol or salt in a volume that is acceptable for parenteral administration. As with oral feeding, an injection dosage form may be administered once per day, although it is contemplated that shorter or longer periods between doses also could be used.

Factors affecting the preferred dosage regimen may include, for example, the type (e.g., species and breed), age, size, sex, diet, activity, and condition of the intended recipient; the type of administration used (e.g., oral via feed, oral via drinking water, subcutaneous implant, other parenteral route, etc.); pharmacological considerations, such as the activity, efficacy, pharmacokinetic, and toxicology profiles of the particular composition administered; and whether the zilpaterol or salt is being administered as part of a combination of active ingredients. Thus, the preferred amount of the zilpaterol or salt can vary, and, therefore, can deviate from the typical dosages set forth above. Determining such dosage adjustments is generally within the skill of those in the art using conventional means.

It is contemplated that the zilpaterol or salt composition may be administered to the intended recipient a single time. In general, however, the composition is administered over time. In some embodiments where the animal recipient is a livestock animal, for example, the zilpaterol or salt is administered daily for at least about 2 days, more typically daily for from about 10 to about 60 days, and still more typically daily for from about 20 to about 40 days. In some particular embodiments, the composition is administered daily for from about the last 10 to about the last 60 days of the finishing period, or from about the last 20 to about the last 40 days of the finishing period. The term "finishing period" refers to the later stage of the growing period for an animal. During this period, livestock animals are typically confined in a feedlot. In some embodiments where the livestock animal is a bovine animal, this period lasts for from about 90 to about 225 days, and depends on, for example, the starting body weight of the animal. There is typically a withdrawal period following the finishing period in which no zilpaterol or salt thereof is administered. The length of this withdrawal period may depend on, for example, the type (e.g., species and breed), age, weight, activity, and condition of the recipient animal, as well as the maximum acceptable residue concentration in the meat of the animal.

EXAMPLES

The following examples are merely illustrative of embodiments of the invention, and not limiting to the remainder of this disclosure in any way.

Example 1

Preparation of 8,9-dihydro-2H,7H-2,9a-diazabenzo[cd]azulene-1,6-dione

Part A. Preparation of chloro 2,3-dihydro-2-oxo-1H-benzimidazol-1-butanoate

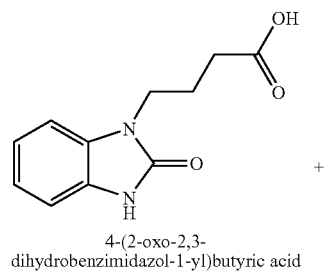

4-(2-oxo-2,3-dihydrobenzimidazol-1-yl)butyric acid 4-(2-Oxo-2,3-dihydrobenzimidazol-1-yl)butyric acid (50 g; 0.227 mol), N,N-dimethylformamide (1.84 g; 0.025 mol; 0.11 eq), and dichloromethane (480 g; 5,652 mol; 24.89 eq) were charged to a stirred-tank reactor. Oxalyl chloride (31.12 g; 0.245 mol; 1.08 eq) was then dosed at 10-20° C. over a 1-hour period while stirring. The resulting mixture was then stirred at 10-20° C. for an additional hour. All the above steps were conducted under a $N_2$ atmosphere.

Part B. Preparation of 8,9-dihydro-2H,7H-2,9a-diazabenzo[cd]azulene-1,6-dione.

The reaction product mixture from Part A was added to a slurry of aluminum chloride (100 g; 0.75 mol, 3.3 eq) in dichloromethane (320 g; 3.768 mol; 16.59 eq) over 2-5 hours at 60° C. and a pressure of 2.7 bar (absolute) in a stirred-tank reactor that allowed HCl gas to escape through an overpressure vent. The resulting slurry was stirred for an additional hour at that temperature, and then cooled to 12° C. In a separate stirred-tank reactor, water (800 g; 44.407 mol; 195.59 eq.) and aqueous 32.5% HCl (118 g; 1.052 mol HCl; 4.63 eq. HCl) were mixed. This mixture was cooled to 0° C., and the gas in the headspace was evacuated to 300 mbar (absolute). The slurry from the first reactor was then added portion-wise to the second reactor, whereby the temperature increased to 10-15° C. under distillation of dichloromethane. The first reactor was rinsed with additional dichloromethane (25 g; 0.294 mol; 1.3 eq), which was then added to the second

Example 2

Preparation of 4,5-dihydro-imidazo[4,5,1-jk][1]benzazepin-2,6,7[1H]-trione-6-oxime.

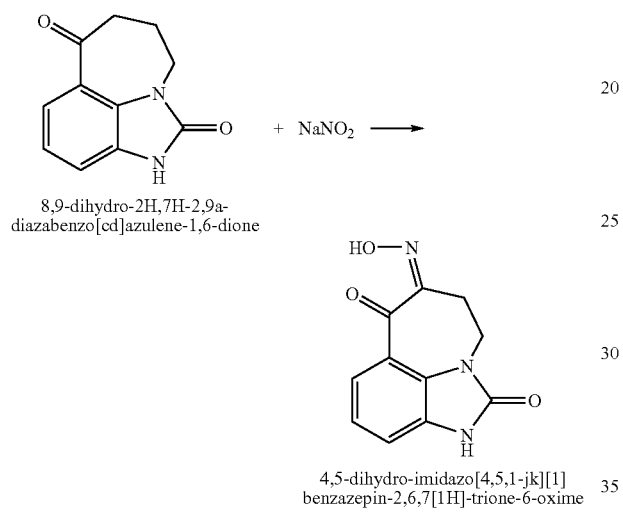

8,9-Dihydro-2H,7H-2,9a-diazabenzo[cd]azulene-1,6-dione (50 g; 92.4% purity; 0.228 mol) prepared in accordance with the procedure in Example 1 was dried and mixed with isopropanol (7.23 g; 0.12 mol; 0.53 eq) and water (3.01 g; 0.167 mol; 0.73 eq) (in alternative experiments and in production, 8,9-dihydro-2H,7H-2,9a-diazabenzo[cd]azulene-1,6-dione prepared in accordance with the procedure in Example 1 was instead used as centrifuge-wet material without the addition of water and isopropanol). The resulting wet 8,9-dihydro-2H-7H-2,9a-diazabenzo[cd]azulene-1,6-dione was combined with sodium nitrite (19.05 g at 99.3% purity; 0.274 mol; 1.2 eq) and N,N-dimethylformamide (800 g; 10.945 mol; 47.9 eq) in a stirred-tank reactor. The mixture was heated to 50° C., and then 32% HCl (41.65 g; 0.366 mol HCl; 1.6 eq HCl) was added over a 30 minute period. Toward the end of the HCl addition (i.e., after greater than 1 eq HCl had been added), the temperature quickly increased to 60-70° C. After all the HCl was added, the mixture was stirred at 60° C. for an additional 30 minutes. The mixture then was cooled to 35° C. over a 2-hour period. Next, water (224.71 g; 12.473 mol; 54.6 eq) was added over a 2-hour period. The resulting mixture was then cooled to 0° C. over a 2-hour period, and maintained at that temperature for 2 hours. Afterward, the solid 4,5-dihydro-imidazo[4,5,1-jk][1]benzazepin-2,6,7[1H]-trione-6-oxime product was removed by filtration and washed 4 times with water (70.1 ml each time; 15.566 mol total; 68.13 eq total) and once with acetone (115.9 g; 99.9% purity; 1.994 mol; 8.73 eq). All the above steps were conducted under a $N_2$ atmosphere.

Example 3

Scale-up Preparation of 8,9-dihydro-2H,7H-2,9a-diazabenzo[cd]azulene-1,6-dione

Part A. Preparation of chloro 2,3-dihydro-2-oxo-1H-benzimidazol-1-butanoate

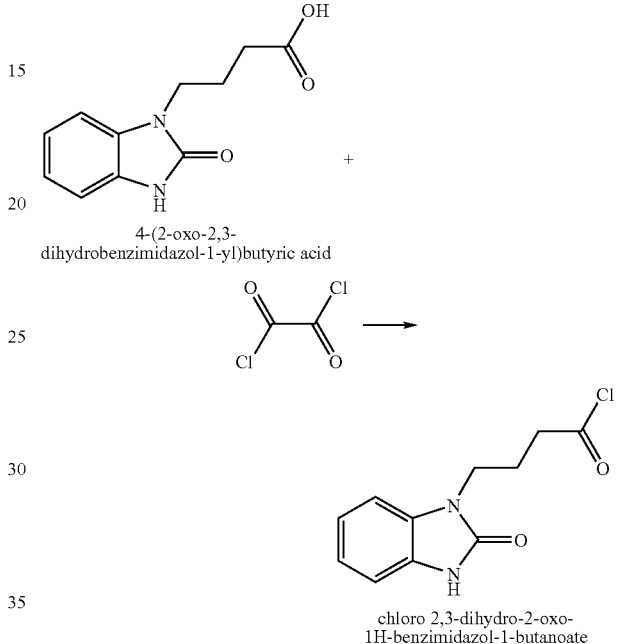

Dichloromethane (3772 L) and then 4-(2-oxo-2,3-dihydrobenzimidazol-1-yl)butyric acid (525 kg; 2.4 kmol) were charged to a stirred-tank reactor, followed by N,N-dimethylformamide (21 L). The resulting mixture was cooled to 10° C. Afterward, oxalyl chloride (326.8 kg)) was dosed at 10-15° C. over 2-3 hours while stirring. The resulting mixture was then stirred at 15-20° C. for an additional 1-3 hours. All the above steps were conducted under a $N_2$ atmosphere. Conversion was checked by in-process control ("IPC").

Part B. Preparation of 8,9-dihydro-2H,7H-2,9a-diazabenzo[cd]azulene-1,6-dione.

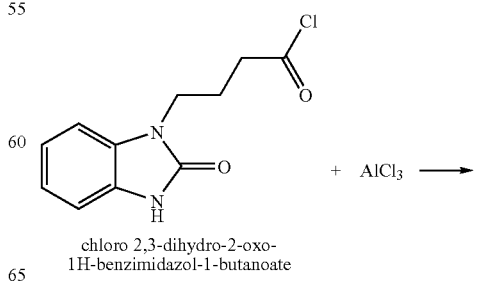

chloro 2,3-dihydro-2-oxo-1H-benzimidazol-1-butanoate + $AlCl_3$ →

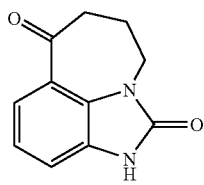

8,9-dihydro-2H,7H-2,9a-
diazabenzo[cd]azulene-1,6-dione

Aluminum chloride (1050 kg) and dichloromethane (2403 L) at 10-20° C. were charged to a stirred-tank reactor, followed by additional dichloromethane (112 L) at 10-20° C. to rinse the reactor. The reactor was then pressurized with N₂ to 2.7 bar (absolute), and heated to 58-60° C. Next, the product mixture from Part A was added over 2-5 hours. The resulting slurry was stirred for an additional 1-2 hours, and then cooled to 10-20° C. Afterward, the pressure was released. In a second stirred-tank reactor at 5° C., water (3675 L) was charged, followed by aqueous 33% HCl (452 L). This mixture was cooled to 0° C., and the gas in the headspace was evacuated to 270-470 mbar (absolute). About half the content from the first reactor was added to the second reactor at from 5-20° C. The mixture was maintained at 10-30° C. for an additional 30-90 minutes. In parallel to and following the transfer, distillation of dichloromethane occurred. The line between the two reactors was rinsed with dichloromethane (150 ml). The resulting rinse and the contents in the second reactor were transferred to a thud stirred-tank reactor. The transfer line between the second and third reactors was rinsed with water (200 L). This rinse also was charged to the third reactor. Water (3675 L) at 5° C. and 33% HCl (452 L) were then added to the second reactor. The resulting mixture was cooled to 0° C., and the pressure in the headspace was set to between 270-470 mbar (absolute). The second half of the content from the first reactor was then added to the second reactor at 5-20° C. This mixture was maintained at 10-30° C. for an additional 30-90 minutes. In parallel to and following the transfer, distillation of dichloromethane occurred. The line between the first and second reactors was rinsed with dichloromethane (150 ml). The resulting rinse and the contents in the second reactor were transferred to the third reactor. The transfer line between the second and third reactors was then rinsed with water (200 L). This rinse was charged to the third reactor. In the third reactor, the dichloromethane was further distilled at 30-40° C. under atmospheric pressure. When the distillation was complete, the suspension was cooled to 0-5° C., and then centrifuged in two parts. Each of the resulting cakes was washed with four times water (390 L for each wash) and once with isopropanol (508 L) at 0-5° C. All the above steps were conducted under a N₂ atmosphere.

Example 4

Scale-up of Preparation of 4,5-dihydro-imidazo[4,5,1-jk][1]benzazepin-2,6,7[1H]-trione-6-oxime.

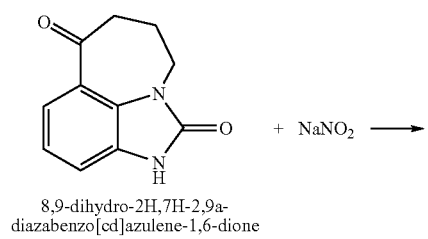

8,9-dihydro-2H,7H-2,9a-
diazabenzo[cd]azulene-1,6-dione

+ NaNO₂ →

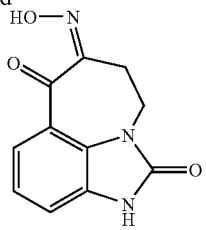

4,5-dihydro-imidazo[4,5,1-jk][1]
benzazepin-2,6,7[1H]-trione-6-oxime

At 20° C., N,N-dimethylformamide (7068 L) was charged to a stirred-tank reactor, followed by 8,9-dihydro-2H,7H-2,9a-diazabenzo[cd]azulene-1,6-dione (450 kg total wet material, approximately 405 kg pure) prepared in accordance with the procedure in Example 3. The addition funnel was rinsed with N,N-dimethylformamide (105 L), and the rinse was charged to the reactor. The resulting mixture was heated at 45° C. until all the 8,9-dihydro-2H,7H-2,9a-diazabenzo[cd]azulene-1,6-dione was in solution. IPC was used to check the amount of pure 8,9-dihydro-2H,7H-2,9a-diazabenzo[cd]azulene-1,6-dione in the mixture, and, from that measurement (together with the mass of wet 8,9-dihydro-2H,7H-2,9a-diazabenzo[cd]azulene-1,6-dione and N,N-dimethylformamide), the exact amount of 8,9-dihydro-2H,7H-2,9a-diazabenzo[cd]azulene-1,6-dione was calculated, which, in turn, was used to calculate the amounts of N,N-dimethylformamide (17.3 kg/kg), sodium nitrite (0.412 kg/kg) and HCl 33% (0.873 kg/kg). For the duration of the IPC, the mixture was cooled to 20° C. Next, sodium nitrite (167 kg, based on 405 kg 8,9-dihydro-2H,7H-2,9a-diazabenzo[cd]azulene-1,6-dione) was added. The addition funnel was rinsed with N,N-dimethylformamide (105 L), and the rinse was charged to the reactor. The temperature was then increased to 45° C. Subsequently, additional N,N-dimethylformamide was charged in the amount calculated earlier (97 L, based on having a total of 7375 L DMF for 405 kg of 8,9-dihydro-2H,7H-2,9a-diazabenzo[cd]azulene-1,6-dione). Next, the resulting mixture was warmed to 48° C., and then 33% HCl (353 kg, based on the batch size) was added over 1 hour, causing the temperature to increase to 60-65° C. by the end of the addition. The mixture was then stirred at 60° C. for another 30 minutes. Next, the mixture was cooled to 45° C. over 1-2 hours. The resulting mixture was transferred into a second reactor. The first reactor was subsequently rinsed with N,N-dimethylformamide (105 L), and the rinse was charged to the second reactor. Water (2000 L) was then added over a 2-hour period at 38° C. The resulting mixture was cooled to 0° C. over 2-3 hours, and then stirred at that temperature for another 2-8 hours. Afterward, the mixture was centrifuged at 0° C., and the resulting cake was washed with three times with water (810 L each time), washed with acetone (1010 L), and dried at 65° C. under vacuum. All the above steps, except for the IPC, were conducted under a N₂ atmosphere.

Example 5

Preparation of Zilpaterol

Part A. Formation of Aminoalcohol Potassium Salt from Ketooxime

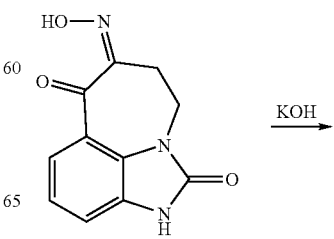

KOH →

-continued

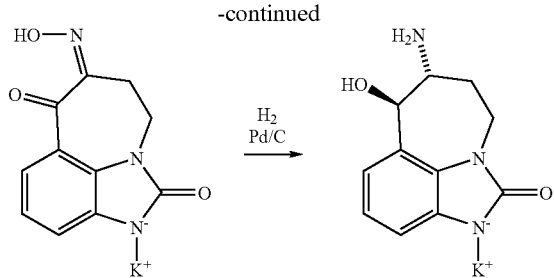

A stirred-tank reactor was purged 3 times with $N_2$ between high pressure (3 bar, absolute) and low pressure (1 bar, absolute) for 10 minutes each. Then a pressure of 0.9 bar (absolute) was established. Water (790 kg) was then charged to the reactor, followed by 4,5-dihydro-imidazo[4,5,1-jk][1]benzazepin-2,6,7[1H]-trione-6-oxime (255 kg) prepared in accordance with Example 4. The reactor contents were then heated to 40° C. Next, 45% KOH (214 kg) was continuously charged to the reactor, causing 4,5-dihydro-imidazo[4,5,1-jk][1]benzazepin-2,6,7[1H]-trione-6-oxime to form the corresponding potassium salt, which, in turn, dissolved (this could be visually verified). The reactor was then charged with active charcoal (13 kg). The resulting mixture was then stirred for 30 minutes at 40° C. The resulting mixture was filtered through a filter loop for one hour to remove the active charcoal. The mixture was then cooled to 15° C. A 5% palladium-on-carbon catalyst (25.5 kg, Johnson-Matthey) was then charged to the reactor. The reactor was then rinsed with water (50 kg). The resulting mixture in the reactor was stirred for 2-6 hours at 40° C. and a $H_2$ pressure of 5-10 bar (absolute). Afterward, the reactor was vented over 30 minutes, and the reaction was analyzed using HPLC. The contents were then filtered in a filter loop for 90 minutes. The filter cake was washed with water (50 L), and removed to recover palladium. The filtered solution was analyzed via HPLC to confirm complete conversion, and then used in the next step.

Part B. Formation of zilpaterol-HOAc.

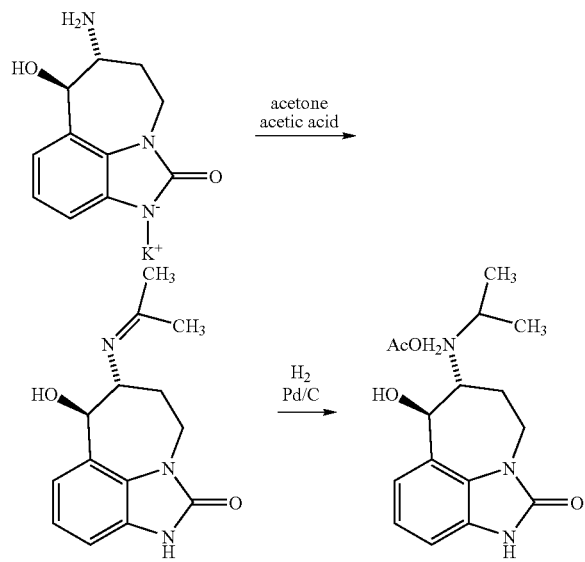

The solution from Part A was cooled to 30° C. Acetone (625 L) was then charged to the reactor. Acetic acid was added to adjust the pH to 7.5 (a pH of from about 7 to about 8 is preferred). The resulting mixture was then cooled to 15° C. Next, a 5% platinum-on-carbon catalyst (21.3 kg, Degussa) was charged to the reactor, followed by water (50 kg) to rinse the reactor. The head space was purged 3 times with $H_2$ between a high pressure of 5 bar (absolute) and a low pressure of 1 bar (absolute) for 15 minutes each. Then a hydrogen pressure of 9.0 bar (absolute, for hydrogenation) was established. The mixture was heated to 70° C. over 1 hour while being stirred, and then maintained at that temperature for an additional hour while being stirred. The reactor was then vented, and the headspace was purged with $N_2$. The reaction was analyzed using HPLC. Acetic acid (8 kg) was then charged to the reactor, and the resulting mixture was cooled to 30° C. More acetic acid was added to adjust the pH to 6.8. The mixture was then transferred through a filter loop for 1 hour while being maintained at 30° C. The resulting cake was washed with 7% aqueous acetic acid (75 L). The filtered solution was transferred to another stirred-tank reactor to be used in the next step.

Part C. Formation of Zilpaterol Free Base

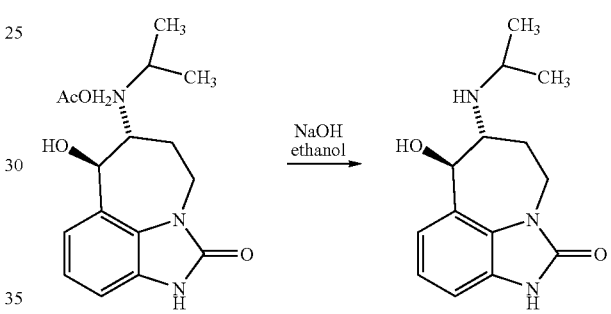

The stirred-tank reactor containing the product from Part B was purged 3 times with $N_2$ between high pressure (2 bar, absolute) and low pressure (1 bar, absolute) for 10 minutes each. Then a pressure of 0.9 bar (absolute) was established. Next, the mixture was concentrated by distillation to 30-70%. The concentrated mixture was cooled to 65° C. Ethanol (331 L) was charged to the reactor, and the resulting mixture was cooled to 50° C. The pH was adjusted to 10 using 25% NaOH. This caused zilpaterol free base to precipitate. The temperature was decreased to 0° C. to facilitate the precipitation, and maintained at that temperature for an additional hour. The solids were filtered off, and washed with water (700 L).

Example 6

Synthesis of an HCl Salt of the Zilpaterol

The free base of zilpaterol is dissolved in ethanol. Subsequently, ethyl acetate saturated with HCl is added. The resulting mixture is vacuum-filtered to obtain a crude product containing the HCl salt of the zilpaterol. The crude product is dissolved in hot methanol. Ethyl acetate is then added, and the mixture is filtered to obtain the final HCl salt product.

Example 7

First Illustration of a Contemplated Suitable Dosage Form

A tablet is prepared containing 2.5 or 5 mg of the HCl salt of Example 6, and sufficient excipient of lactose, wheat starch, treated starch, rice starch, talc, and magnesium stearate for a final weight of 100 mg.

Example 8

Second Illustration of a Contemplated Suitable Dosage Form

Granules are prepared containing 12.5 or 25 of the HCl salt of Example 6 in each daily dose of granules.

Example 9

Third Illustration of a Contemplated Suitable Dosage Form

The HCl salt of Example 6 is crystallized using the methodology discussed U.S. Pat. No. 5,731,028 for making crystalline racemic trans zilpaterol. Less than 5% of the crystals have a size of less than 15 μm, and at least 95% of the crystals have a size of less than 250 μm. A premix of the crystalline HCl salt secured to a 300-800 μm corn cob support is then obtained using the methodology discussed in European Patent 0197188 (incorporated by reference into this patent). The concentration of the HCl salt in the premix is 3% (by weight).

\* \* \* \* \* \* \* \*

The words "comprise," "comprises," and "comprising" in this patent (including the claims) are to be interpreted inclusively rather than exclusively. This interpretation is intended to be the same as the interpretation that these words are given under United States patent law.

The words "process" and "method" are used interchangeably in this patent.

All references cited in this patent are incorporated by reference into this patent.

The above detailed description of preferred embodiments is intended only to acquaint others skilled in the art with the invention, its principles, and its practical application so that others skilled in the art may adapt and apply the invention in its numerous forms, as they may be best suited to the requirements of a particular use. This invention, therefore, is not limited to the above embodiments, and may be variously modified.

We claim:

1. A process for making a zilpaterol intermediate, or a salt thereof, wherein the process comprises:
    making chloro 2,3-dihydro-2-oxo-1H-benzimidazol-1-butanoate (or a salt thereof) by a process comprising reacting 4-(2-oxo-2,3-dihydrobenzimidazol-1-yl)butyric acid (or a salt thereof) with at least one chlorinating agent selected from the group consisting of oxalyl chloride, phosgene, and triphosgene; or
    making 4,5-dihydro-imidazo[4,5,1-jk][1]benzazepin-2,6,7[1H]-trione-6-oxime (or a salt thereof) by a process comprising reacting 8,9-dihydro-2H,7H-2,9a-diazabenzo[cd]azulene-1,6-dione (or a salt thereof) with an inorganic nitrite.

2. The process according to claim 1, wherein the process comprises making chloro 2,3-dihydro-2-oxo-1H-benzimidazol-1-butanoate (or a salt thereof) by a process comprising reacting 4-(2-oxo-2,3-dihydrobenzimidazol-1-yl)butyric acid (or a salt thereof) with at least one chlorinating agent selected from the group consisting of oxalyl chloride, phosgene, and triphosgene.

3. The process according to claim 1, wherein the process comprises making 4,5-dihydro-imidazo[4,5,1-jk][1]benzazepin-2,6,7[1H]-trione-6-oxime (or a salt thereof) by a process comprising reacting 8,9-dihydro-2H,7H-2,9a-diazabenzo[cd]azulene-1,6-dione (or a salt thereof) with an inorganic nitrite.

4. A process for making zilpaterol, or a salt thereof, wherein the process comprises:
    reacting 8,9-dihydro-2H,7H-2,9a-diazabenzo[cd]azulene-1,6-dione (or a salt thereof) with an inorganic nitrite to form 4,5-dihydro-imidazo[4,5,1-jk][1]benzazepin-2,6,7[1H]-trione-6-oxime (or a salt thereof);
    converting the 4,5-dihydro-imidazo[4,5,1-jk][1]benzazepin-2,6,7[1H]-trione-6-oxime (or a salt thereof) to an aminoalcohol salt;
    wherein the aminoalcohol salt corresponds in structure to Formula (WO-2):

(WO-2)

converting the aminoalcohol salt to an isopropylideneamino compound (or a salt thereof); and
    reacting the isopropylideneamino compound (or a salt thereof) with $H_2$ in the presence of a hydrogenation catalyst,
    wherein the isopropylideneamino compound corresponds in structure to Formula (WO-1):

(WO-1)

5. A process for making zilpaterol, or a salt thereof, wherein:
    an isopropylideneamino compound or a salt thereof is reacted with $H_2$ in the presence of a hydrogenation catalyst, wherein at least a portion of the isopropylideneamino compound or a salt thereof is made by a process comprising combining an aminoalcohol salt with acetone and acetic acid, wherein the aminoalcohol salt corresponds in structure to Formula (WO-2):

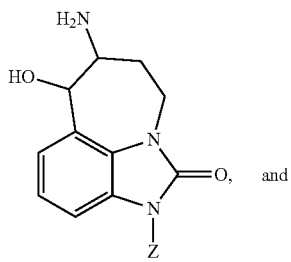 (WO-2)

Z is a cation.

6. The process according to claim 2, wherein the process comprises:
    making 8,9-dihydro-2H,7H-2,9a-diazabenzo[cd]azulene-1,6-dione or a salt thereof by a process comprising reacting the chloro 2,3-dihydro-2-oxo-1H-benzimidazol-1-butanoate (or a salt thereof) with a Lewis acid.

7. The process according to claim 6, wherein the Lewis acid comprises $AlCl_3$.

8. The process according to claim 6, wherein the process comprises:
    making chloro 2,3-dihydro-2-oxo-1H-benzimidazol-1-butanoate (or a salt thereof) by a process comprising reacting 4-(2-oxo-2,3-dihydrobenzimidazol-l-yl)butyric acid (or a salt thereof) with oxalyl chloride;
    making a product mixture comprising 8,9-dihydro-2H-2,9a-diazabenzo[cd]azulene-1,6-dione (or a salt thereof) by a process comprising:
        combining chloro 2,3-dihydro-2-oxo-1H-benzimidazol-1-butanoate (or a salt thereof) with $AlCl_3$, and combining the resulting mixture with an acid;
        separating 8,9-dihydro-2H,7H-2,9a-diazabenzo[cd]azulene-1,6-dione from the product mixture; and
        separating $Al(OH)_3$ from at least a portion of the remaining product mixture by a process comprising combining at least a portion of the remaining product mixture with a base.

9. The process according to claim 1, wherein 4-(2-oxo-2,3-dihydrobenzimidazol-1-yl)butyric acid (or a salt thereof) is reacted with the chlorinating agent in the presence of dichloromethane.

10. The process according to claim 1, wherein 4-(2-oxo-2,3-dihydrobenzimidazol-1-yl)butyric acid (or a salt thereof) is reacted with the chlorinating agent in the presence of a catalytic amount of dimethylformamide.

11. The process according to claim 1, wherein the chlorinating agent comprises oxalyl chloride.

12. The process according to claim 1, wherein the inorganic nitrite comprises a nitrite salt.

13. The process according to claim 12, wherein the nitrite salt comprises $NaNO_2$.

14. The process according to claim 2, wherein the process is utilized to make zilpaterol.

15. The process according to claim 3, wherein the process is utilized to make zilpaterol.

* * * * *